(12) United States Patent
Shawver et al.

(10) Patent No.: US 6,884,418 B1
(45) Date of Patent: Apr. 26, 2005

(54) USE OF LIGAND-MIMICKING AGENTS AND ANTI-NEOPLASTIC DRUGS IN CANCER THERAPY

(75) Inventors: Laura K. Shawver, Alameda, CA (US); John W. Brandis, Hercules, CA (US); Elaina Mann, San Leandro, CA (US); Miriam E.C. Hancock, Oakland, CA (US); Ronald P. Mischak, Palo Alto, CA (US); John J. Monahan, Orinda, CA (US)

(73) Assignee: Berlex Laboratories, Inc., DE (US)

( * ) Notice: Subject to any disclaimer, the term of this patent is extended or adjusted under 35 U.S.C. 154(b) by 1826 days.

(21) Appl. No.: 07/644,361

(22) Filed: Jan. 18, 1991

Related U.S. Application Data

(63) Continuation-in-part of application No. 07/473,570, filed on Feb. 1, 1990, now abandoned, which is a continuation-in-part of application No. 07/389,846, filed on Aug. 4, 1989, now abandoned.

(51) Int. Cl.$^7$ ............................................. A61K 39/395

(52) U.S. Cl. .................. 424/155.1; 424/130.1; 424/133.1; 424/141.1; 435/344; 530/388.15; 530/388.8

(58) Field of Search ........................... 424/130.1, 133.1, 424/141.1, 155.1; 530/388.15, 388.8; 435/344

(56) References Cited

U.S. PATENT DOCUMENTS

| | | | |
|---|---|---|---|
| 4,017,471 A | 4/1977 | Davies | 260/112 |
| 4,093,607 A | 6/1978 | Sela et al. | |
| 4,140,707 A | 2/1979 | Cleare et al. | 260/429 |
| 4,172,124 A | 10/1979 | Koprowski et al. | |
| 4,177,263 A | 12/1979 | Rosenberg et al. | 424/131 |
| 4,699,877 A | 10/1987 | Cline et al. | 435/6 |
| 4,753,894 A | 6/1988 | Frankel et al. | |
| 4,935,341 A | 6/1990 | Bargmann et al. | |
| 4,968,603 A | 11/1990 | Slamon et al. | |

FOREIGN PATENT DOCUMENTS

| | | |
|---|---|---|
| EP | 0 359 282 | 9/1989 |
| JP | 62-108157 | 11/1985 |
| WO | WO89/10412 | 4/1988 |
| WO | WO89/06692 | 1/1989 |
| WO | WO89/10412 | 4/1989 |
| WO | WO 89/06692 | 7/1989 |
| WO | WO89/10412 | 11/1989 |

OTHER PUBLICATIONS

Harris et al. TibTeln Vol 11. p. 42 1993.*
Osband Immunology Today 11(5) 1990 p. 193.*
Cancer Res. Read et al. 1990, 50(13) 39 47–51 (abstract).*
"Immunotherapy and Monoclonal Ab." p. 183–187 *Genes & Cancer* 1990 Wiley & Sons.*

Identification of a Phosphoprotein Specifically Induced by the Transforming DNA of Rat Neuroblastomas, Lakshmi Charan Padhy et al., Cell, vol. 20, pp. 865–871, Apr. 1982.
Monoclonal antibodies identify a cell–surface antigen associated with an activated cellular oncogene, Jeffrey A. Drebin et al., Nature, Vol, 312, pp. 545–548, Dec. 6, 1984.
The neu oncogene: an erb–B–related gene encoding a 185,000–M tumour antigen, Alan L. Schecter et al., Nature, vol. 312, pp. 513–516, Dec. 6, 1984.
The Product of the Human c–erbB–2 Gene: A 185–Kilodalton Glycoprotein with Tyrosine Kinase Activity, Tetsu Aklyama et al., Science, vol. 232, pp. 1644–1646, 1986.
Expression of the c–erbB–2 Protein in Normal and Transformed Cells, William J. Gullick et al., Int. J. Cancer: 40, pp. 246–254, 1987.
Abstract JP 2150293–A2.
U.S. Appl. No. 06/836,414, King et al., filed Mar. 5, 1986.
U.S. Appl. No. 07/389,920, Stuart et al., filed Aug. 4, 1989.
Hudziak R. et al., "p185 $^{HER2}$ Monoclonal Antibody Has Antiproliferative Effects In Vitro and Sensitizes Human Breast Tumor Cells to Tumor Necrosis Factor", *Mol. Cell. Biol.*, 9:1165–1172 (1989).
Lidor, Y. et al., "Alkylating Agents and Immunotoxins Exert Synergistic Antitumor Activity Against Ovarian Cancer Cell Lines", *Proceedings of the American Association for Cancer Research*, 30:401 (1989).
Hurwitz, E. et al., "A Synergistic Effects Between Anti–Idiotype Antibodies and Anti–Neoplastic Drugs in the Therapy of a Murine B–Cell Tumor", *Oncogene*, 2:387–394 (1988).
Drebin, J.A. et al., "Monoclonal antibodies specific for the neu oncogene product directly mediate anti–tumor effects in vivo", *Oncogene*, 2:387–394 (1988).

(Continued)

*Primary Examiner*—Sheela J. Huff
(74) *Attorney, Agent, or Firm*—Millen, White, Zelano & Branigan, P.C.

(57) ABSTRACT

This invention is directed toward novel synergistic combinations of ligand-mimicking agents specific to the c-erbB-2 protein and anti-neoplastic drugs or agents, which can be used to treat a mammalian host, usually a human, suspected of having cancer or tumor cells by administering the combination in a therapeutically- or synergistically-effective amount. The drug combinations cytotoxic to tumor cells comprise an anti-neoplastic agent and a molecule, that is not conjugated to the anti-neoplastic agent, that binds the tumor cells and induces an increase in the phosphorylation of c-erbB-2 protein when placed in contact with the tumor cells. Alternatively, the drug combination cytotoxic to tumor cells may comprise an anti-neoplastic agent and a molecule, that is not conjugated to the anti-neoplastic agent, that binds the tumor cells and causes down modulation or internalization of c-erbB-2 protein. The anti-neoplastic drug is preferably an alkylating agent, most preferably cisplatin. This combination is particularly effective for inhibiting the growth of breast and ovarian tumor cells. Methods for killing target tumor cells are contemplated by contacting the target cells with the novel drug combinations, methods for treating mammals by administering therapeutic amounts of the drug combinations are also contemplated.

21 Claims, 22 Drawing Sheets

OTHER PUBLICATIONS

Langton, B. et al., "The development and characterization of antibodies to different regions of the c–erbB–2 protein on breast tumor tissue and cell lines" (Abstract and Poster) American Association for Cancer Research Conference held May 24–27, 1989.

Slamon, D.J. et al., "Studies of the HER–2/neu Proto–oncogene in Human Breast and Ovarian Cancer", Science, 244:707–712 (1989).

Slamon, D.J. et al., "Human Breast Cancer: Correlation of Relapse and Survival with Amplification of the HER–2/neu Oncogene", Science, 235:177–182 (1987).

Yarden, Y. et al., "Experimental approaches to hypothetical hormones: Detection of a candidate ligand of the neu protooncogene", Proc. Natl. Acad. Sci. USA, 86:3179–3183 (1989).

King, C.R. et al., "Amplification of a Novel v–erbB–Related Gene in a Human Mammary Carcinoma", Science, 229–974–976 (1985).

Schechter, A.L. et al, "The neu Gene: An erbB–Homologous Gene Distinct from and Unlinked to the Gene Encoding the EGF Receptor", Science, 229:976–978 (1985).

Semba, K. et al., "A v–erbB–related protooncogene, c–erbB–2, is distinct from the c–erbB–1/epidermal growth factor–receptor gene and is amplified in a human salivary gland adenocarcinoma", Proc. Natl. Acad. Sci. USA, 82:6497–6501 (1985).

Coussens, L. et al., "Tyrosine Kinase Receptor with Extensive Homology to EFG Receptor Shares Chromosomal Location with neu Oncogene", Science, 230:1132–1139 (1985).

Drebin, J.A. et al., "Down–Modulation of an Oncogene Protein Product and Reversion of the Transformed Phenotype by Monoclonal Antibodies", Cell, 41:695–706 (1985).

Lupu, R. et al., "Direct Interaction of a Ligand for the erbB2 Oncogene Product with the EGF Receptor and p185 $^{erbB2}$", Science, 249:1552–1555 (1990).

Kraus, M.H. et al., "Overexpression of the EGF receptor–related proto–oncogene erbB–2 in human mammary tumor cell lines by different molecular mechanisms", The EMBO Journal, 6:605–610 (1987).

Connelly, P.A. et al., "The epidermal growth factor receptor and the product of the neu protooncogene are members of a receptor tyrosine phosphorylation cascade", Proc. Natl. Acad. Sci. USA, 87:6054–6057 (1990).

Hudziak, R.M. et al., "Amplified expression of the HER2/ERBB2 oncogene induces resistance to tumor necrosis factor $\alpha$ in NIH 3T3 cells", Proc. Natl. Acad. Sci. USA, 85:5102–5106 (1988).

Williams, D.E. et al., "Identification of a Ligand for the c–kit Proto–Oncogene", Cell, 63:167–174 (1990).

Nocka, K. et al., "Candidate ligand for the c–kit transmembrane kinase receptor: KL, a fibroblast derived growth factor stimulates mast cells and erythroid progenitors", The EMBO Journal, 9:3287–3294 (1990).

Yarden, Y. et al., "Human proto–oncogene c–kit: a new cell surface receptor tyrosine kinase for an unidentified ligand", The EMBO Journal, 6:3341–3351 (1987).

Scanlon, K.J. et al., "Biochemical basis for cisplatin and 5–fluorouracil synergism in human ovarian carcinoma cells", Proc. Natl. Acad. Sci. USA, 83:8923–8925 (1986).

Scanlon, K.J. et al., "Molecular Basis of Cisplatin Resistance in Human Carcinomas: Model Systems and Patients", Anticancer Research, 9:1301–1312 (1989).

Aggarwal, S.K. et al., "Effect of Cisplatin on the Plasma Membrane Phosphatase Activities in Ascites Sarcoma–180 Cells: A Cytochemical Study", Journal of Histochemistry and Cytochemistry, 31:307–317 (1985).

Defize, L.H. et al., "Dissociation of cellular responses to epidermal growth factor using anti–receptor monoclonal antibodies", The EMBO Journal, 5:1187–1192 (1986).

Zick, Y. et al., "The Role of Antireceptor Antibodies in Stimulating Phosphorylation of the Insulin Receptor", Journal of Biological Chemistry, 259:4396–4400 (1984).

Yarden, J., "Agonistic antibodies stimulate the kinase encodes by the neu Protooncogene in living cells by the oncogenic mutant is constitutively active", Proc. Natl. Acad. Sci. USA, 87:2569–2573 (1990).

Aboud–Pirak et al. "Efficacy of Antibodies to Epidermal Growth Factor Receptor Against KB Carcinoma In Vitro and in Nude Mice" J. Nat. Cancer Inst. 80:1605–1611 (1988).

Hurwitz et al. "A Synergistic Effect Between Anti–Idiotype Antibodies and Anti–Neoplastic Drugs in the Therapy of a Murine B–Cell Tumor" Int. J. Cancer 37:739–745 (1986).

Drebin et al. "Monoclonal antibodies reactive with distinct domains of the neu oncogene–encoded p185 molecule exert synergistic anti–tumor effects in vivo" Oncogene 2:273–277 (1988).

Slamon et al. "Human Breast Cancer: Correlation of Relapse and Survival with Amplification of the HER–2/neu Oncogene" Science 235:177–182 (1987).

Langton et al. "An Antigen Immunologically Related to the External Domain of gp185 is Shed from Nude Mice Tumors Overexpressing the c–erbB–2 (HER–2/neu)" Cancer Res. 51: 2593–2598 (1991).

DeNardo et al. "Radioimmunotherapy for breast cancer: MoAb biokinetics to treatment protocols" Poster Abstract, 4th International Workshop on Monoclonal Antibodies and Breast Cancer held Nov. 5–6, 1990.

Waldmann "Monoclonal Antibodies in Diagnosis and Therapy" Science 252:1657–1662 (1991).

Hancock et al. A Monoclonal Antibody against the c–erB–2 Protein Enhances the Cytotoxicity of cis–Diamminedichloro–platinum against Human Breast and Ovarian Tumor Cell Lines Cancer Res. 51:4575–4580 (1991).

Houghton et al. "Monoclonal Antibodies: Potential Applications to the Treatment of Cancer" Seminars in Oncology 13:165–179 (1986).

Houghton et al. "The Suitability and Use of Human Tumor Xenografts" Rodent Tumor Models in Experimental Cancer Therapy Chapter 42, Edited by Robert F. Kallman, Ph.D., Pergamon Press.

Corbett et al. "Rodent Models in Experimental Chemotherapy" Rodent Tumor Models in Experimental Cancer Therapy Chapter 50, Edited by Robert F. Kallman, Ph.D., Pergamon Press.

Lidor et al. "Alkylating Agents and Immunotoxins Exert Synegistic Antitumor Activity Against Ovarian Cancer Cell Lines" Proceeddings of the American Association for Cancer Research 30:401 (1989).

Hurwitz et al. "A Synergistic Effect Between Anti–Idiotype Antibodies and Anti–Neopolastic Drugs in the Therapy of a Murine B–Cell Tumor" Int. J. Cancer 37:739–745 (1986).

Drebin et al. "Monoclonal antibodies reactive with distinct domains of the new oncogene–encoded p185 molecule exert synergistic anti–tumor effects in vivo" Ocogene 2:273–277 (1988).

Drebin et al., "Monoclonal antibodies specific for the neu oncogene product directly mediate anti–tumor effects in vivo" Oncogene 2:387–394 (1988).

Langton et al., "The development and characterization of antibodies to different regions of the c–erB–2 protein on breast tumor tissue and cell lines" (Abstract and Poster) American Association for Cancer Research Conference held May 24–27, 1989.

Slamon et al. "Studies of the HER–2/neu Proto–oncogene in Human Breast and Ovarian Cancer" Science 244: 707–712 (1989).

Slamon et al. "Human Breast Cancer: Correlation of Relapse and Survival with Amplification of the Her–2/neu Oncogene" Science 235:177–182 (1987).

Yarden et al. "Experimental approaches to hypothetical hormones: Detection of a candidate ligand of the neu proto–oncogene" Proc. Natl. Acad. Sci. USA 86:3179–3183 (1989)..

King et al. "Amplification of a Novel v–erB–2 Related Gene in a Human Mammary Carcinoma" Science 229:974–976 (1985).

Schechter et al. The new Gene: An erbB–Homologous Gene Distinct from and Unlinked to the Gene Encoding the EGF Receptor Science 229:976–978 (1985).

Aboud–Pirak et al. "Efficacy of Antibodies to Epidermal Growthh Factor Receptor Against KB Carcinoma In Vitro and in Nude Mice" *J. Nat. Cancer Inst.*80:1605–1611 (1988).

Hudziak et al., "p185 $^{HER2}$ Monoclonal Antibody Has Antiproliferative Effects In Vitro and Sensitizes Human Breast Tumor Cells to Tumor Necrosis Factor"Mol. Cell. Biol. 9: 1165–1172 (1989).

Yarden, Y. et al., "Experimental approaches to hypothetical hormones: Detection of a candidate ligand of the neu protooncogene", *Proc. Natl. Acad. Sci. USA*, 86:3179–3183 (1989).

King, C.R. et al.,"Amplificatioin of a Novel v–erB–Related Gene in a Human Mammary Carcinoma", Science, 229–974–976 (1985).

Schechter, A.L. et al., "The neu Gene: An erB–Homologous Gene Distinct from and Unlinked to the Gene Encoding the EGF Receptor", *Science*, 229:976–978 (1985).

Semba, K. et al., "A v–erB–related protooncogene, c–erB–2, is distinct from the c–erB–1/epidermal growth factor–receptor gene and is amplfied in a human salivary gland adenocarcinoma", *Proc. Natl. Acad. Sci. USA*, 82:6497–6501 (1985).

Coussens, L. et al., "Tyrosine Kinase Receptor with Extensive Homology to EFG Receptor Shares Chromosomal Location with neu Oncogene" *Science*, 230:1132–1139 91985).

Drebin, J.A. et al., "Down–Modulation of an Oncogene Protein Product and Reversion of the Transformed Phenotype by Monoclonal Antibodies", *Cell*, 41:695–706 (1985).

Lupu, R. et al., "Direct Interaction of a Ligand for the erbB2 Oncogene Prtoducts with the EGF Receptor and p185 $^{erbB2"}$, *Science*, 249:1552–1555 (1990).

Kraus, M.H. et al., "Overexpression of the EGF receptor––related proto–oncogene erbB–2 in human mammary tumor cell lines by different molecular mechanisms", *The EMBO Journal*, 6:605–610 (1987).

Connelly, P.A. et al., "The epidermal growth factor receptor and the product of the neu protooncogene are members of a receptor tyrosine phosphorylation cascade", *Proc. Natl. Acad. Sci. USA*, 87:6054–6057 (1990).

Hudziak, R.M. et al., "Amplified expression of the HER2/ERB2 oncogene induces resistance to tumor necrosis factor αin NIH 3T3 cells", *Proc. Natl. Acad. Sci. USA*, 85:5102–5106 (1988).

Williams, D. E. et al., "Identification of a Ligand for the c–kit Proto–Oncogene", *Cell*, 63:167–174 (1990).

Nocka, K. et al., "Candidate ligand for the c–kit transmembrane kinase receptor: KL, a fibroblast derived growth factor stimulates mast cells and erythroid progenitors", *The EMBO Journal*, 9:3287–3294 (1990).

Yarden, Y. et al., "Human proto–oncogene c–kit: a new cell surface receptor tyrosine kinase for an unidentified ligand", *The EMBO Journal*, 6:3341–3351 (1987).

Scanlon, K.J. et al., "Biochemical basis for cisplatin and 5–fluorouracil synergism in human ovaria carcinoma cells", *Proc. Natl. Acad. Sci. USA*, 83:8923–8925 (1986).

Scanlon, K.J. et al., "Molecular Basis of Cisplatin Reistance in Human Carcinomas: Model Systems and Patients", *Anticancer Research*, 9:1301–1312 (1989).

Aggarwal, S.K. et al., "Effect of Cisplatin on the Plasma Membrane Phosphatase Activities in Ascites Sarcoma–180 Cells: A Cytochemical Study", *Journal of Histochemistry and Cytochemistry*, 31:307–317 (1985).

Defize, L.H. et al., "Dissociation of cellular responses to epidermal growth factor using anti–receptor monoclonal antibodies", *The EMBO Journal*, 5:1187–1192 (1986).

Zick, Y. et al., "The Role of Antireceptor Antibodies in Stimulating Phosphorylation of the Insulin Receptor", *Journal of Biological Chemistry*, 259:4396–4400 (1984).

Yarden, J. "Agonistic antibodies stimulate the kinase encodes by the neu Protooncogene in living cells by the oncogenic mutant is constitutively active", *Proc. Natl. Acad. Sci. USA*, 87:2569–2573 (1990).

* cited by examiner

US 6,884,418 B1

USE OF LIGAND-MIMICKING AGENTS AND ANTI-NEOPLASTIC DRUGS IN CANCER THERAPY

RELATED APPLICATIONS

This application is a continuation-in-part of Ser. No. 07/473,570, filed Feb. 1, 1990, now abandoned, which is a continuation-in-part application of Ser. No. 07/389,846, filed Aug. 4, 1989, now abandoned, which are both incorporated by reference herein.

FIELD OF THE INVENTION

This invention relates to compositions and methods for impeding tumor cell growth and, more particularly, relates to synergistic combinations of anti-neoplastic drugs and ligand-mimicking agents reactive with tumor cells and their use to control tumor cell growth.

BACKGROUND OF THE INVENTION

The study of oncogenes holds considerable promise in elucidating the mechanism of the disease of cancer, and leading to improved pharmaceutical treatments. Oncogenes and their products appear to be associated with the transformation of cells to malignancy through growth control pathology. While the occurrence of oncogenes was first detected in retroviruses, it has been established that many viral oncogenes have cellular counterparts (for a review, see Tronick and Aaronson, Oncogenes Growth Regulation and Cancer in *Advances in Second Messenger* and *Phosphoprotein Research*, 28:201 (1988)). While only a small number have a known physiological function, this knowledge has provided important insights about how oncogenes and protooncogenes work in both normal and malignant cells.

Over 50 oncogenes have been thus far identified, many of which have properties of growth factor receptors (e.g., erbB, erbB-2, fms, kit, trk, met, ret, ros, sea, eph, eck, elf, and flg). These properties include an extracellular domain, ligand binding domain, transmembrane region, and an intracellular domain that exhibits tyrosine kinase activity. The erbB gene was found to share strong homology with the epidermal growth factor (EGF) receptor (Downward et al., *Nature*, 307:521–527 (1984)) and fms was shown to be homologous to the receptor for colony stimulating factor-1 (Sherr et al., *Cell*, 41:665–676 (1985)). Recently, ligands for c-erbB-2 (Lupu et al., *Science*, 249:1552–1555 (1990)), and c-kit (Flanagan and Leder, *Cell*, 63:185–194 (1990)); Nocka et al., *EMBO J.*, 9:3287–3294 (1990); Zsebo et al., *Cell*, 63:213–224 (1990)) have been reported.

There is now mounting evidence that tumorigenicity is closely correlated to the presence and level of expression of these cell-surface oncogenes. Both the existence and enhanced expression of the oncogene proteins may result from alterations including genetic rearrangements, point mutations, or amplifications at the deoxyribonucleic acid (DNA), the ribonucleic acid (RNA), or protein levels (Bishop, *Science*, 235:305 (1987); DiFiore, et al. *Science*, 237:178 (1987); Slamon, et al. *Science*, 235:177 (1987); Krause, et al., *The EMBO Journal*, 6:605 (1987); and Der, *Clinical Chemistry*, 33:641 (1987)). While many of these oncogene proteins are present on the surface of some normal cells (such as in the case of c-erbB-2), the amplification or overexpression of oncogenes has been shown to correlate with tumorigenic activity. In fact, the amplification of the c-erbB-2 oncogene indicates a very poor clinical prognosis, especially in breast and ovarian cancer (Slamon, et al., *Science* 235:177 (1987) and Slamon, et al., *Science*, 244:707 (1989)).

A wide range of anti-neoplastic drugs have been identified for cancer therapy. Considerable difficulties, however, are encountered with the use of these drugs because of their toxicity to normal tissue. Monoclonal antibody technology brought with it a promising tool to attempt to specifically target cancer cells. Most of the clinical studies to date using this technology for cancer treatments have been disappointing, however, for many reasons, including the requirement for large doses to deliver sufficient drug to the cancer cells. Such large doses result in toxic side effects largely due to non-specific binding to normal cells and processing of the drugs by the liver. Thus, there exists a continuing need for safer and more effective treatments to eliminate and control tumor cell growth.

SUMMARY OF THE INVENTION

This invention is directed toward novel synergistic combinations of ligand-mimicking agents specific to the c-erbB-2 protein and anti-neoplastic drugs or agents, which can be used to treat a mammalian host, usually a human, suspected of having cancer or tumor cells by administering the combination in a therapeutically- or synergistically-effective amount. The drug combinations cytotoxic to tumor cells comprise an anti-neoplastic agent and a molecule, that is not conjugated to the anti-neoplastic agent, that binds the tumor cells and induces an increase in the phosphorylation of c-erbB-2 protein when placed in contact with the tumor cells. Alternatively, the drug combination cytotoxic to tumor cells may comprise an anti-neoplastic agent and a molecule, that is not conjugated to the anti-neoplastic agent, that binds the tumor cells and causes down modulation or internalization of c-erbB-2 protein. The anti-neoplastic drug is preferably an alkylating agent, most preferably cisplatin. This combination is particularly effective for inhibiting the growth of breast and ovarian tumor cells. Methods for killing target tumor cells are contemplated by contacting the target cells with the novel drug combinations. Methods for treating mammals by administering therapeutic amounts of the drug combinations are also contemplated.

The drug combinations of this invention advantageously permit the administration of significantly reduced levels of toxic chemotherapeutic agents because of the synergistic benefit achieved by the concomitant administration of the ligand-mimicking agent and the chemotherapeutic drug. Further, because the "chemotherapeutic" agent is not conjugated to the ligand-mimicking agent, the distribution of the toxic agent is not linked to the distribution of the ligand-mimicking agent as in the case of immunotoxins. For example, where immunotoxins are employed, the toxin typically gets distributed to nonspecific locations such as to the liver as well as the specific target.

Figure 8:
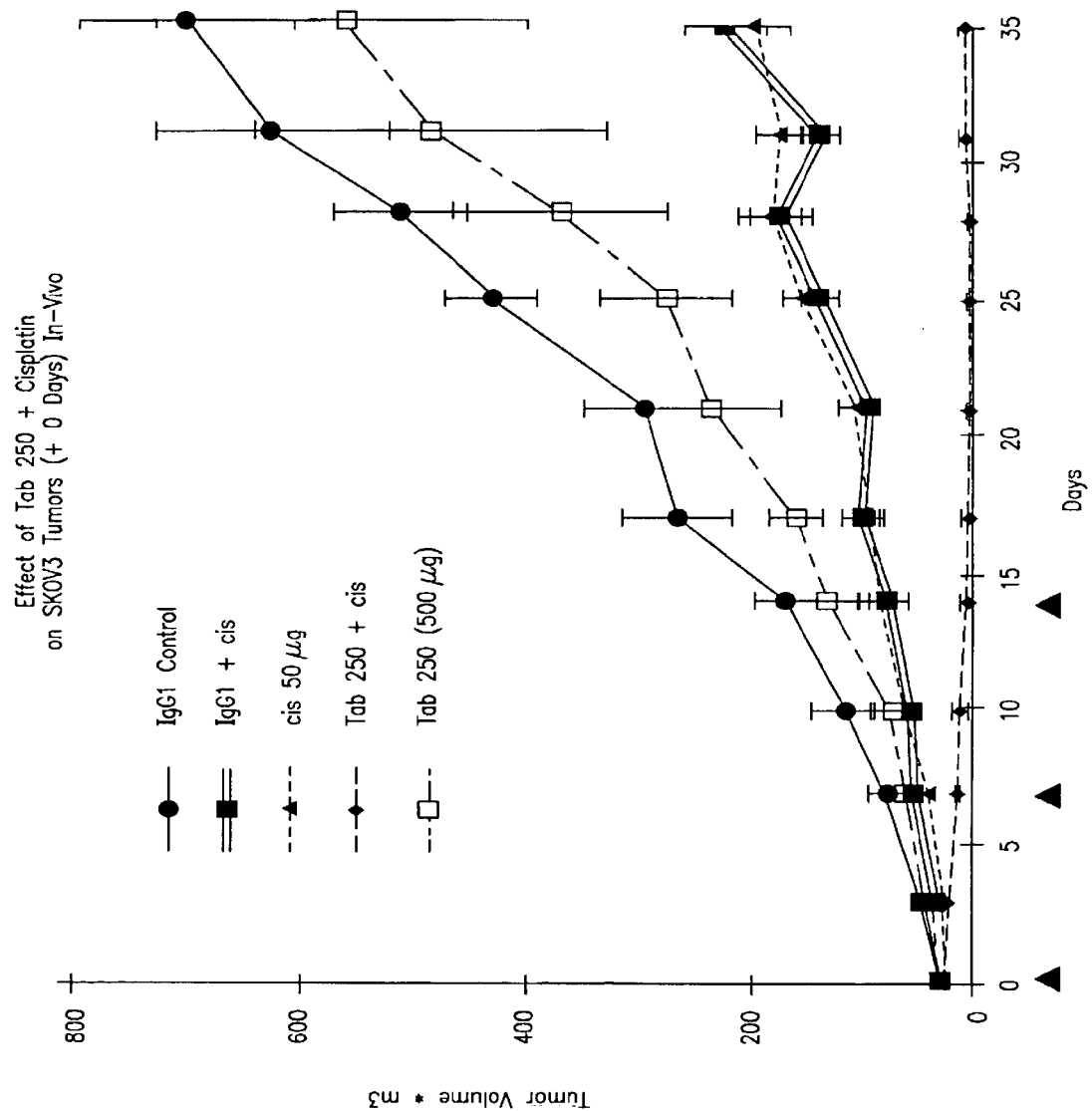
FIGS. 8, 9 and 10 show the synergistic effect of a c-erbB-2 antibody (TAb 250) in combination with cisplatin on human tumor xenografts in athymic mice. For FIG. 8, SKOV3 cells derived from a metastatic ovarian tumor were injected subcutaneously into nude mice. The tumors were grown in the mice, extracted, minced and reimplanted. After one week, the mice were divided into five groups of six mice each and the groups were treated intravenously once a week for three weeks as follows: Group 1—500 $\mu$g of a nonspecific IgG1 isotype control; Group 2—500 $\mu$g of TAb 250 alone; Group 3—50 $\mu$g of cisplatin alone; Group 4—500 $\mu$g of the isotype control plus 50 $\mu$g of cisplatin; and Group 5—500 $\mu$g of TAb 250 plus 50 $\mu$g of cisplatin. Significant inhibition of tumor growth was observed in Group 5.
Figure 9:
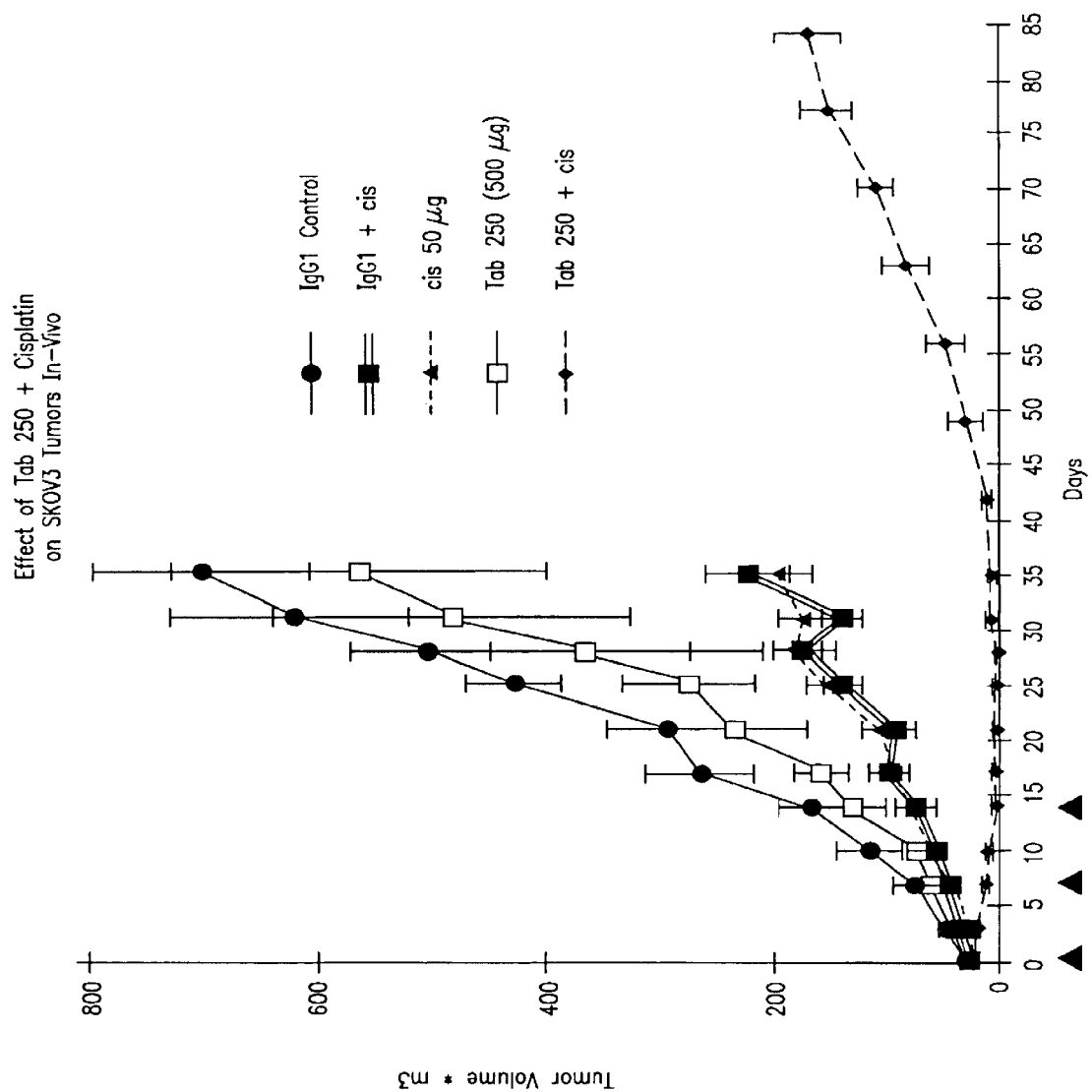

Shown in FIG. 9 are the same mice used in FIG. 8, but the experiment was continued until day 85 with no additional treatments. The tumors previously treated with the c-erbB-2 antibody and cisplatin combination did not begin to grow until day 45. At day 85, the tumors treated with the combination reached a size equivalent to the tumors treated with cisplatin alone at day 35.

Figure 10:
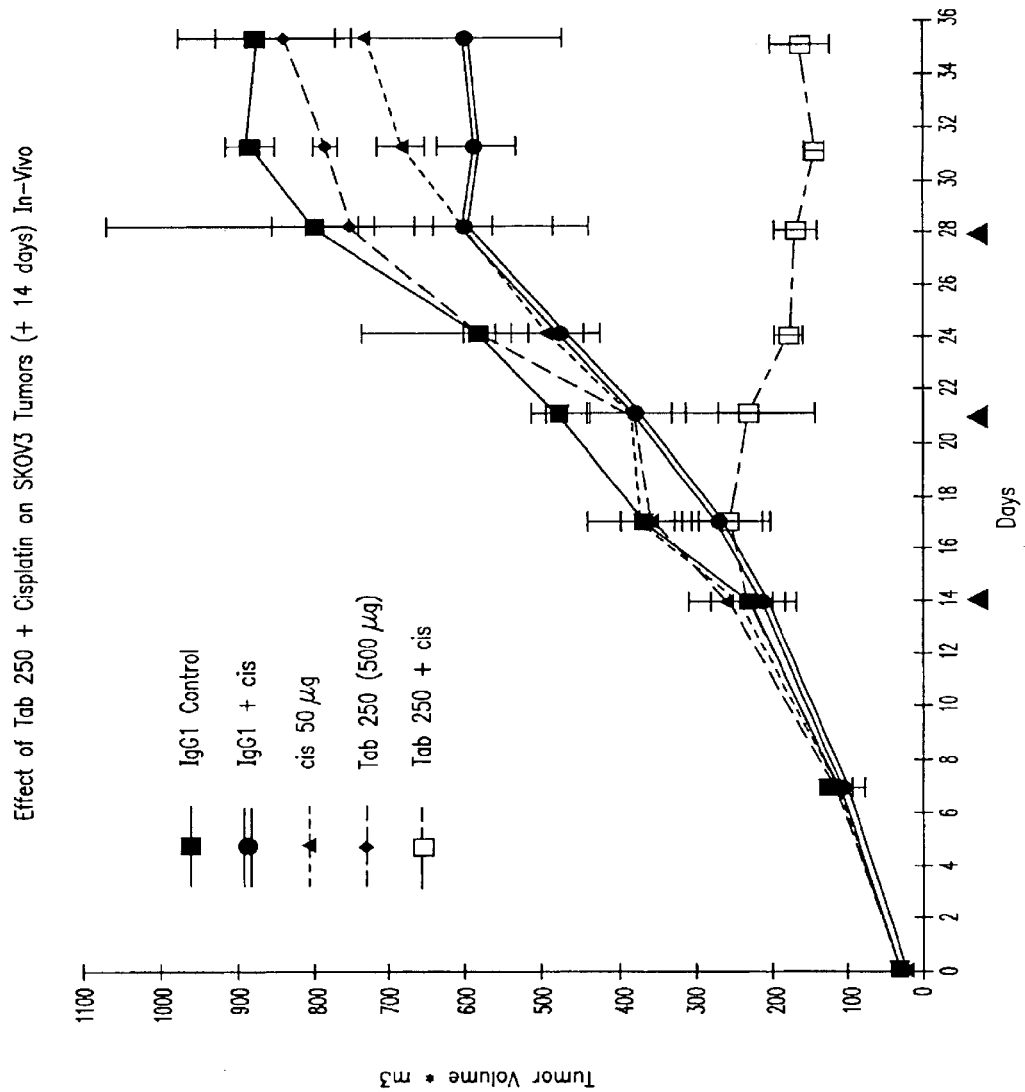

FIG. 10 shows another human tumor xenograft experiment similar to the one conducted as described for FIG. 8. However, following tumor cell implantation the tumors were allowed to grow to a volume of 150–200 mm$^3$ prior to treatment. The tumors were treated once a week for three weeks (on days 14, 21 and 28 as indicated by the arrows) with antibody and cisplatin as described for FIG. 8. Significant inhibition of tumor growth was observed for the mice treated with c-erbB-2 antibody and cisplatin.

Figures 11A, 11B:
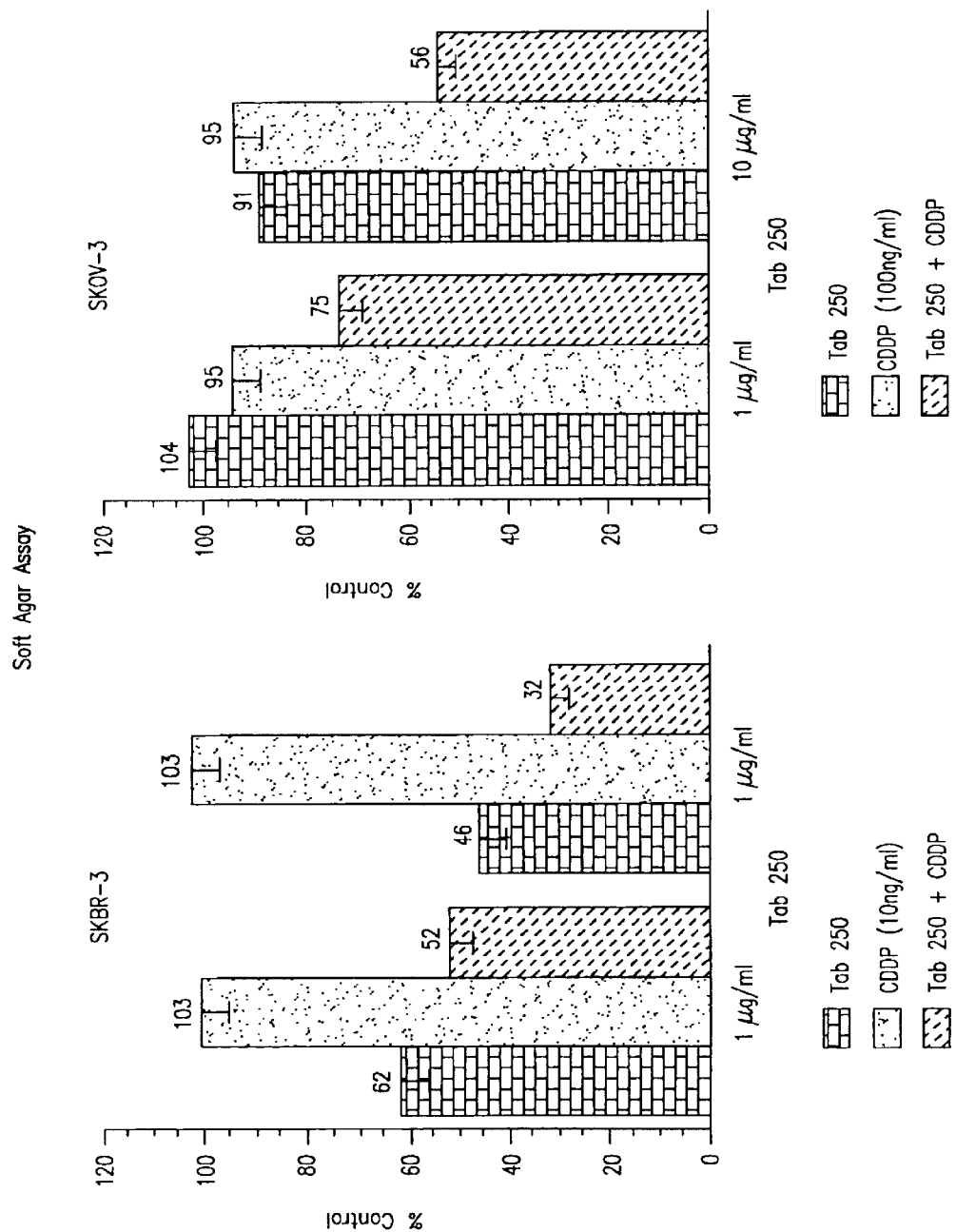

FIG. 11 is a bar graph showing the effects of TAb 250 alone and in combination with cisplatin (CDDP) on the growth of SKBR3 cells (FIG. 11A) and on SKOV3 cells (FIG. 11B) using a soft agar clonogenic assay. Concentrations of 1 $\mu$g/ml and 10 $\mu$g/ml of TAb 250 were used and the data are expressed as a percentage of untreated control colonies formed in soft agar.

Figure 12A:
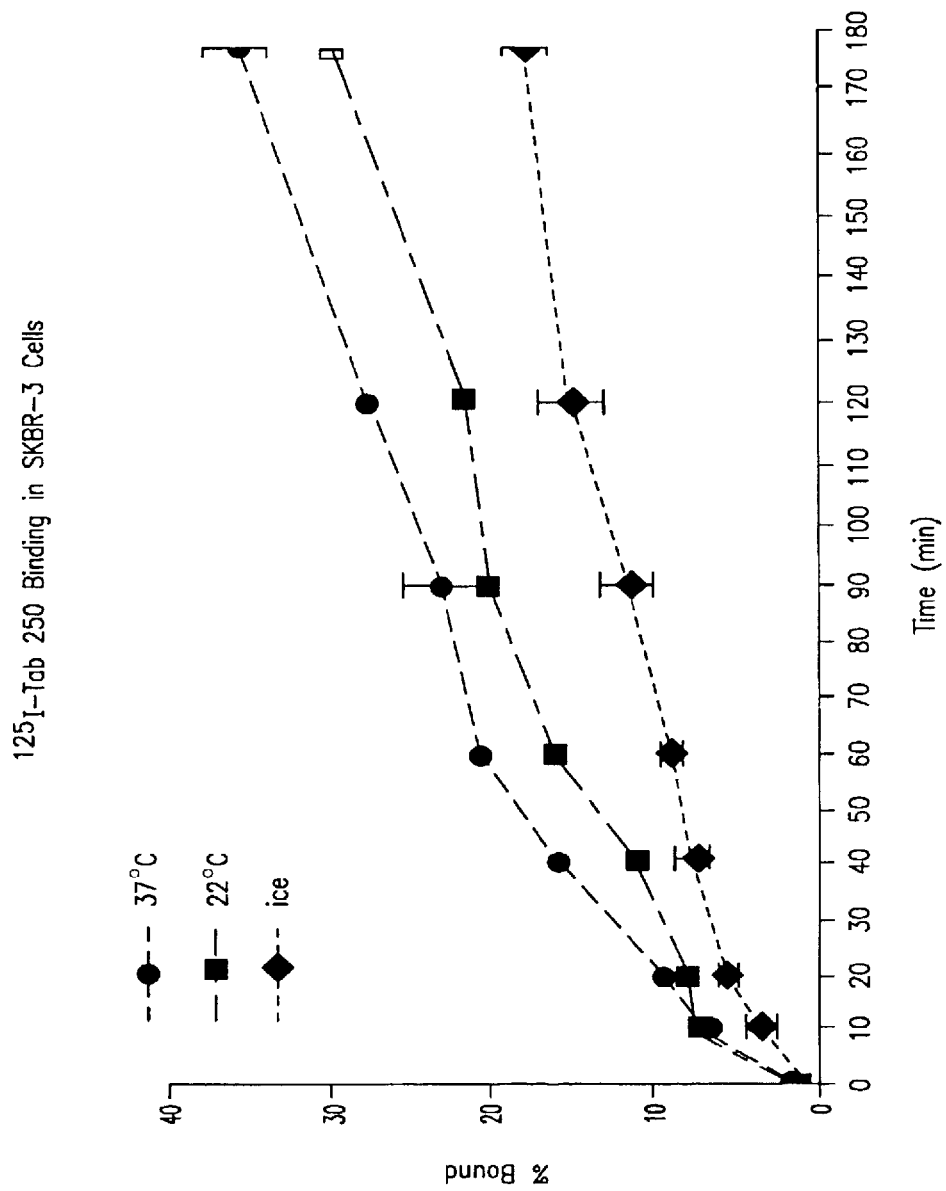
Figure 12B:
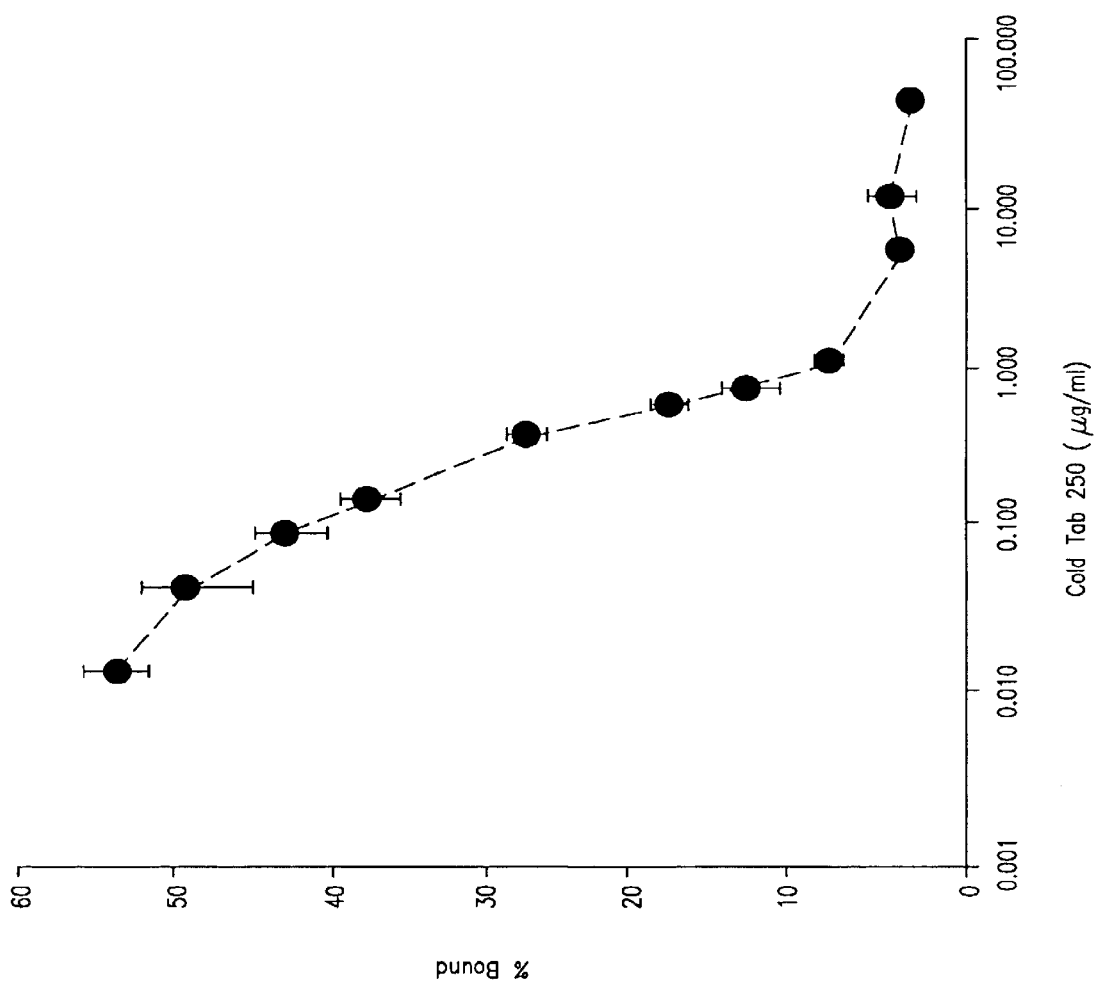
Figure 12C:
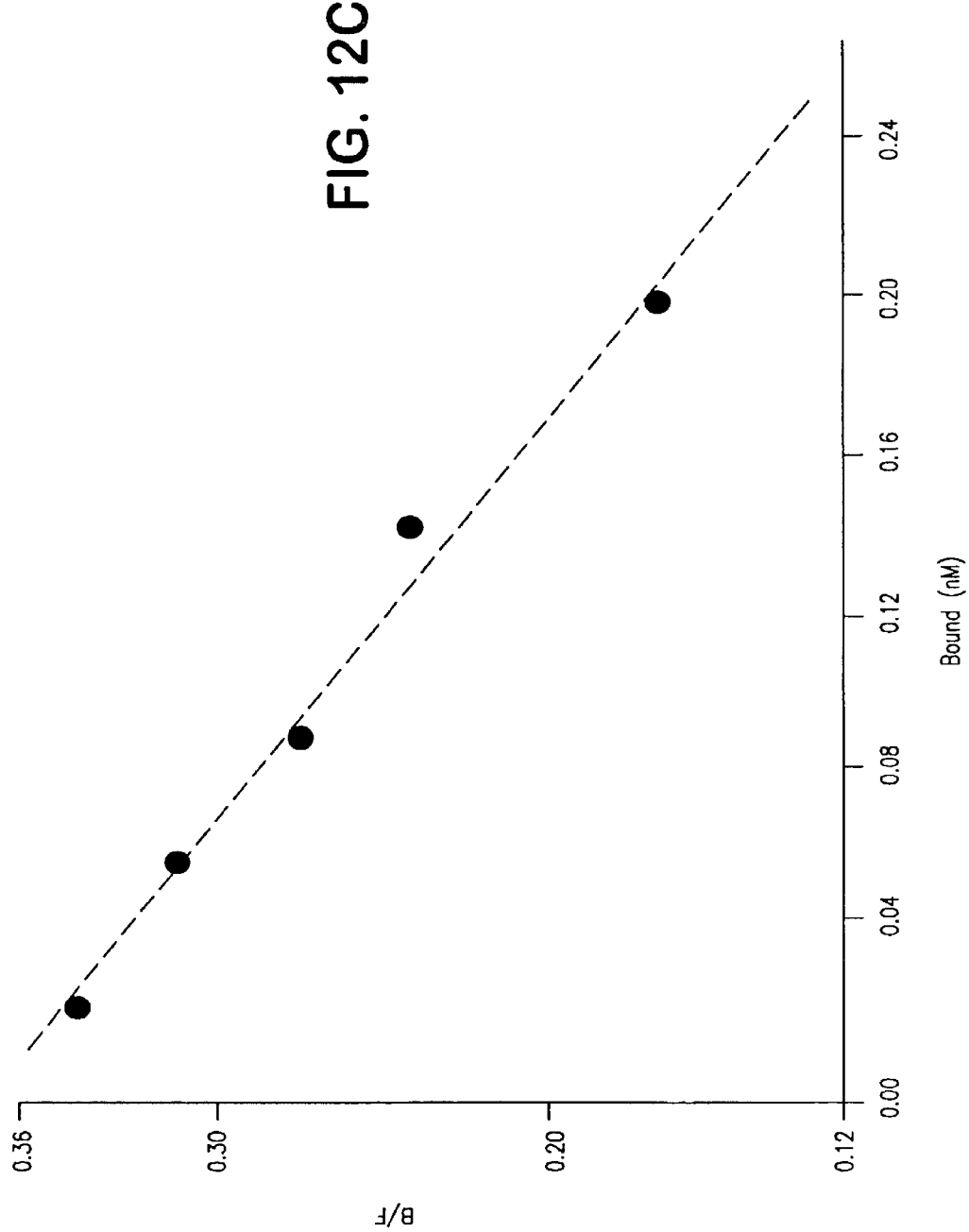

FIG. 12A is a graph showing the time and temperature dependence of $^{125}$I-TAb 250 binding in SKBR3 cells. The time points along the x-axis indicate the time permitted for binding and the graph plots three different curves for assays at 37° C., 22° C. and on ice. FIG. 12B shows the displacement of $^{125}$I-TAb 250 in the presence of increasing amounts of unlabeled TAb 250. FIG. 12C represents a Scatchard plot of displacement data and shows a single class of high affinity binding sites.

Figure 13A:
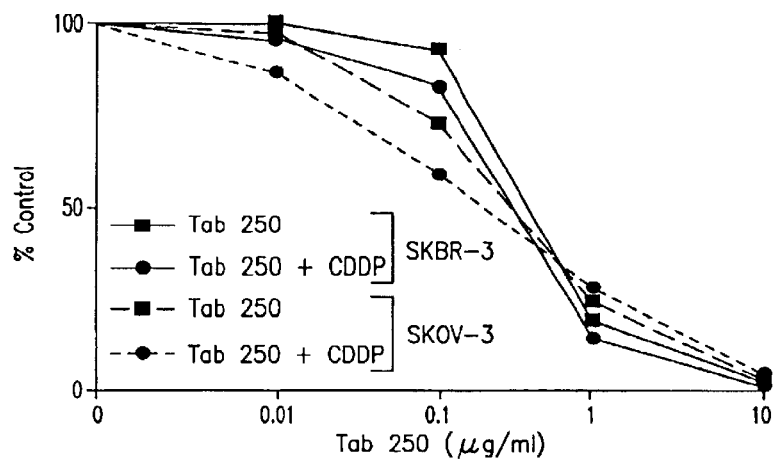
Figure 13B:
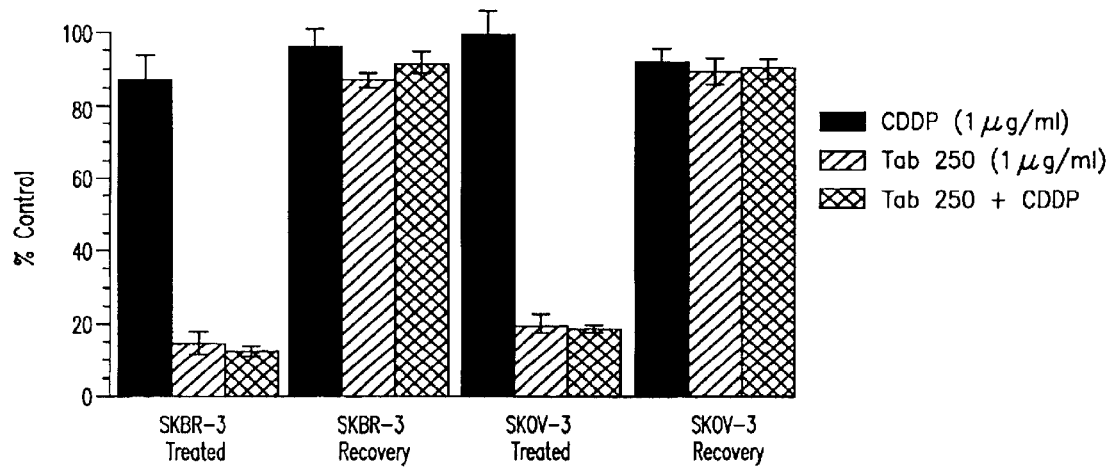
Figure 13C:
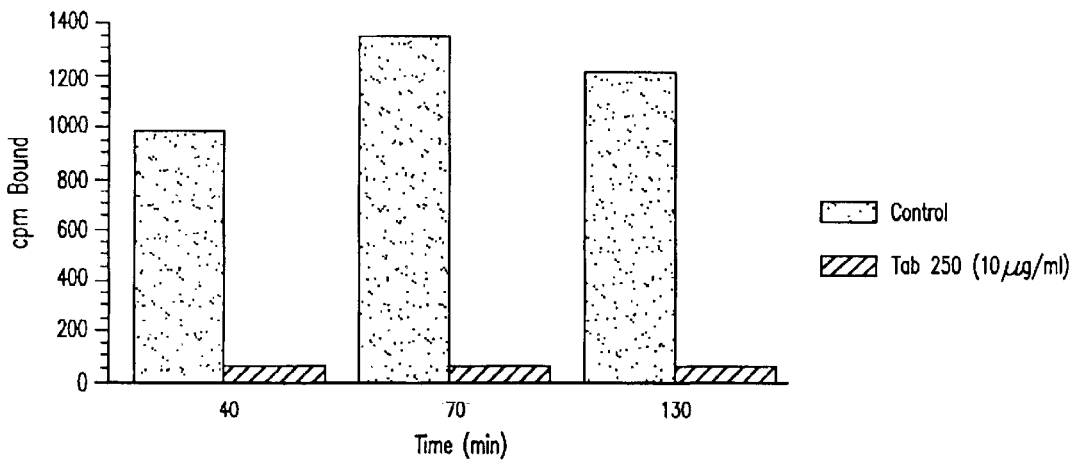

FIGS. 13A, 13B and 13C show down modulation of $^{125}$I-TAb 250 alone or in combination with 1 $\mu$g/ml of cisplatin. The percent of binding is determined after 24 hours of exposure to TAb 250, the cells were then washed and either used immediately in the binding assays (FIG. 13A) or they were allowed to recover in growth medium for 24 hours prior to the binding assay (FIG. 13B). In FIG. 13C, a time course for down modulation is shown for SXBR3 cells.

Figure 14A:
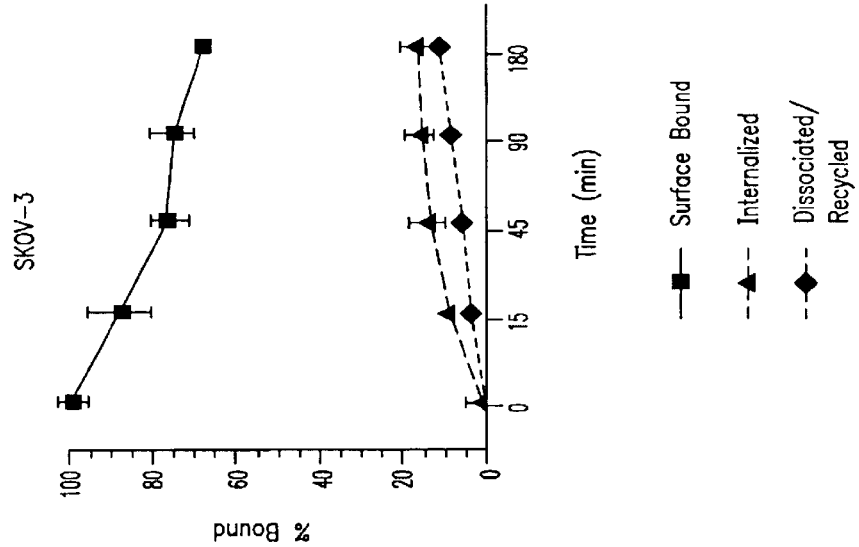
Figure 14B:
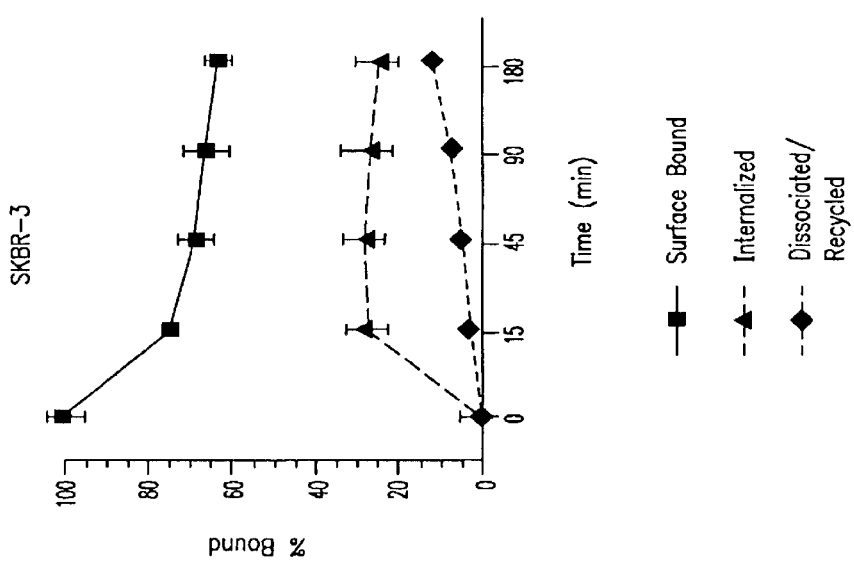

FIGS. 14A and 14B plot the internalization of $^{125}$I-TAb 250 over time in SKBR3 cells (FIG. 14A) and in SKOV3 cells (FIG. 14B) where the amount of antibody bound to the surface of the cells is expressed as a percentage of the initial surface bound antibody.

Figure 15A:
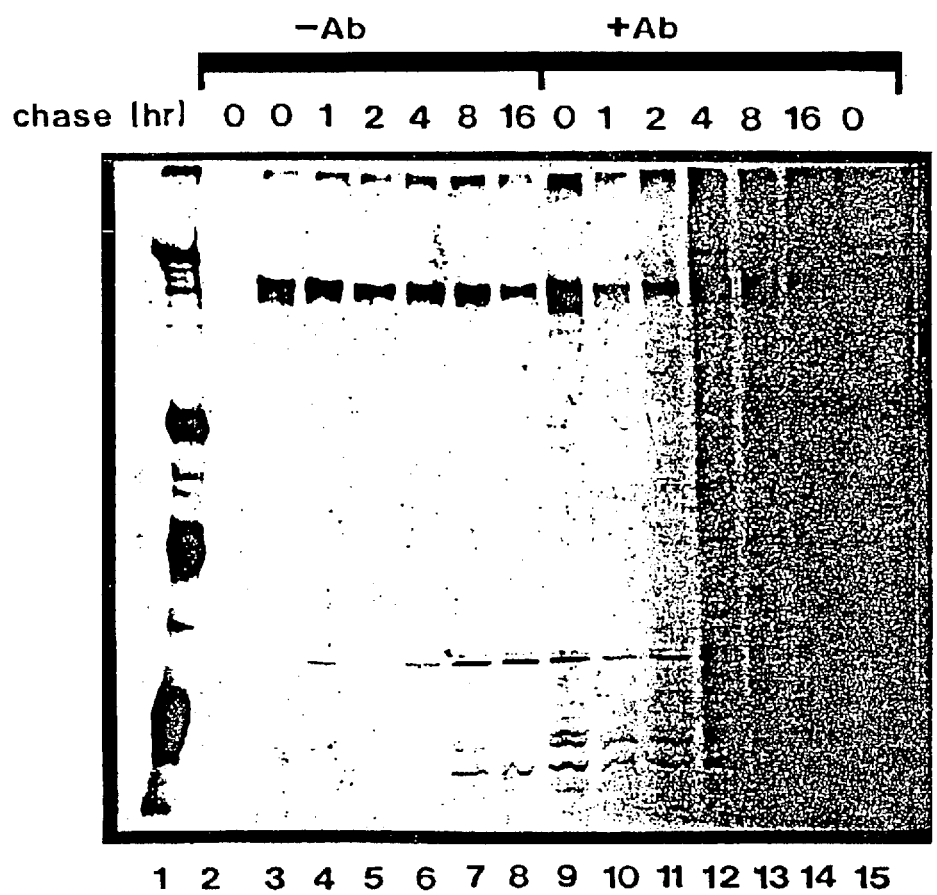
Figure 15B:
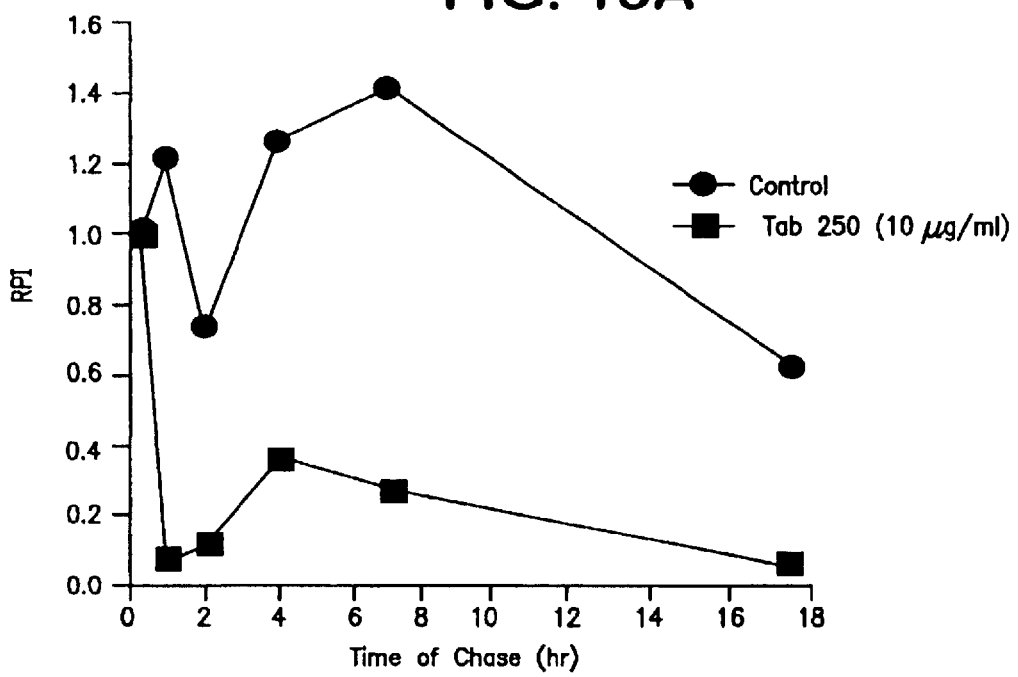

FIG. 15A shows an SDS-PAGE gel of immunoprecipitated SKBR3 cells with either nonimmune IgG (lanes 2 and 15) or TAb 250 (lanes 3–14). Lanes 2–8 represent immunoprecipitants from cells chased in medium alone, while lanes 9–15 represent immunoprecipitants from cells chased in medium containing 10 $\mu$g/ml of TAb 250. The autoradiograph was scanned with a laser densitometer and the relative peak intensity plotted against time of chase as shown in FIG. 15B.

Figure 16:
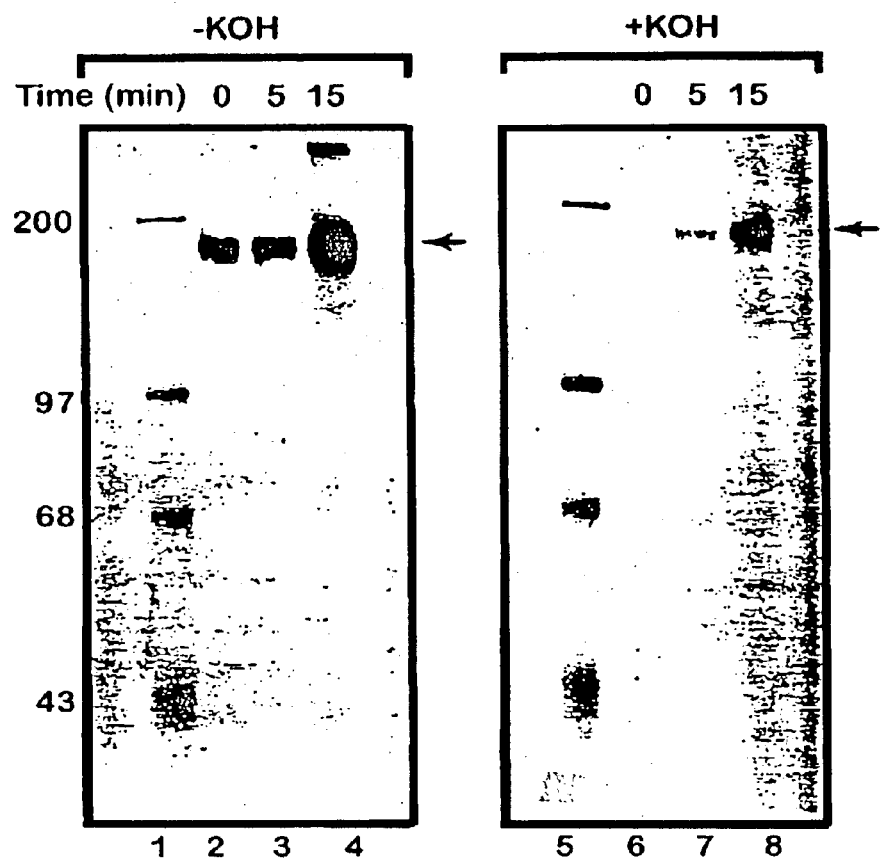

FIG. 16 shows c-erbB-2 receptor phosphorylation in SKBR3 cells labelled with $^{32}$P-orthophosphate and incubated with 10 $\mu$l/ml of TAb 250 for the times indicated. The cells were lysed and immunoprecipitations were carried out using an antibody to the C-terminus of the c-erbB-2 protein, analyzed by SDS-PAGE and autoradiography and then treated with 1M KOH.

Figure 17B:
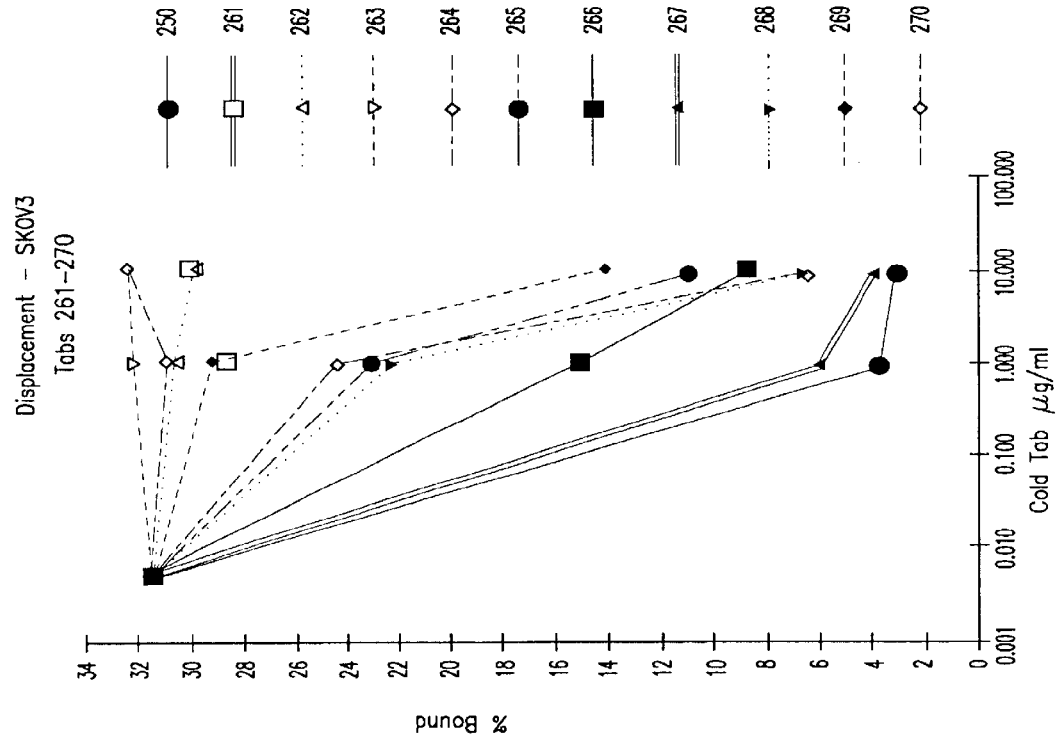
Figure 17A:
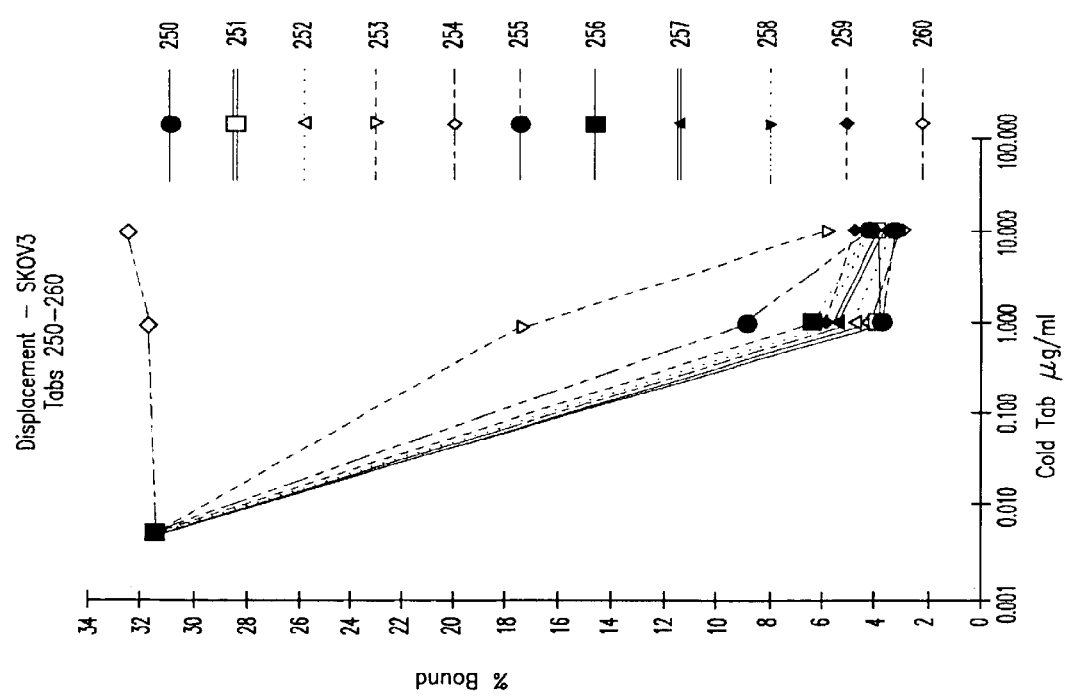

FIGS. 17A and B plot the displacement of $^{125}$I-TAb 250 in a competitive binding assay by several different anti-c-erbB-2 antibodies using SKOV3 cells in a competitive binding assay.

Figure 18:
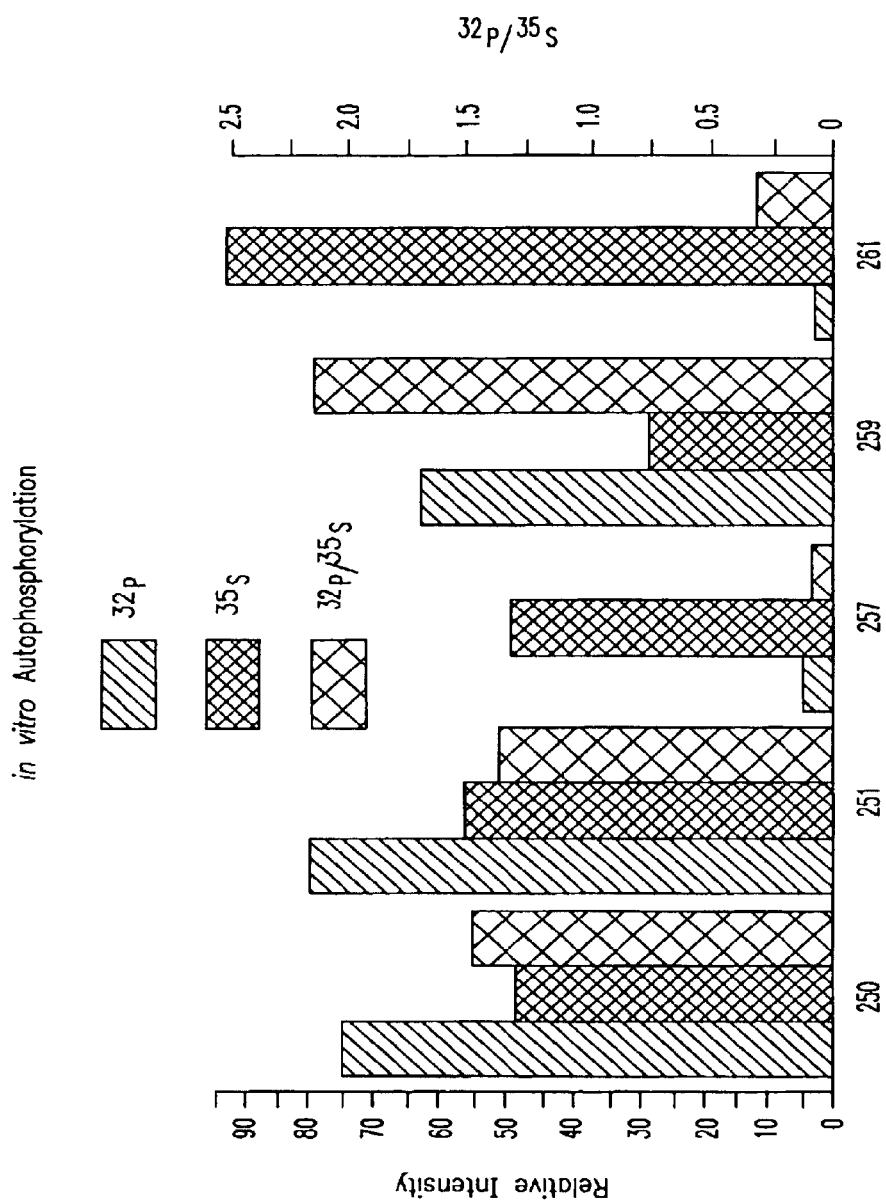

FIG. 18 shows the results of an in vitro autophosphorylation study of five anti-c-erbB-2 antibodies (TAbs 250, 251, 257, 259 and 261) using NIH3T3 cells.

Figure 19:
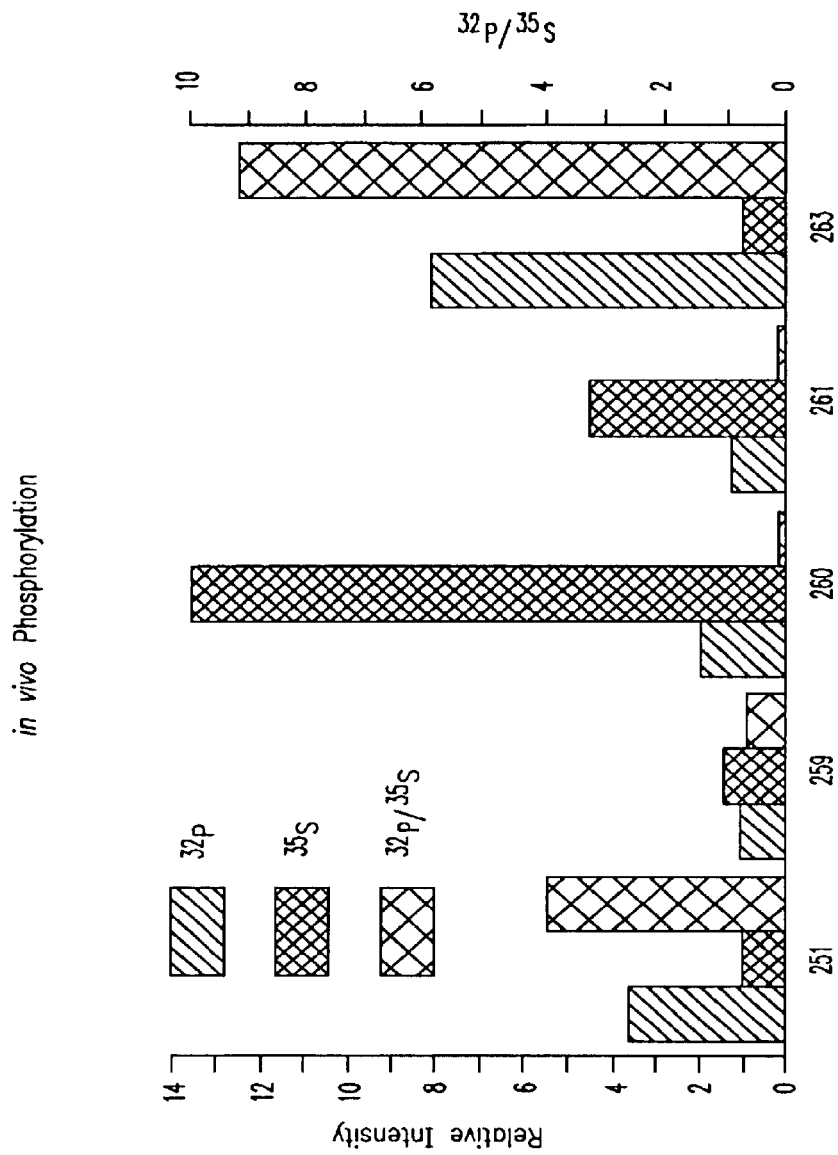

FIG. 19 shows the results of an in vivo phosphorylation study of five anti-c-erbB-2 antibodies (TAbs 251, 259, 260, 261 and 263) using NIH3T3 cells.

Figure 20:
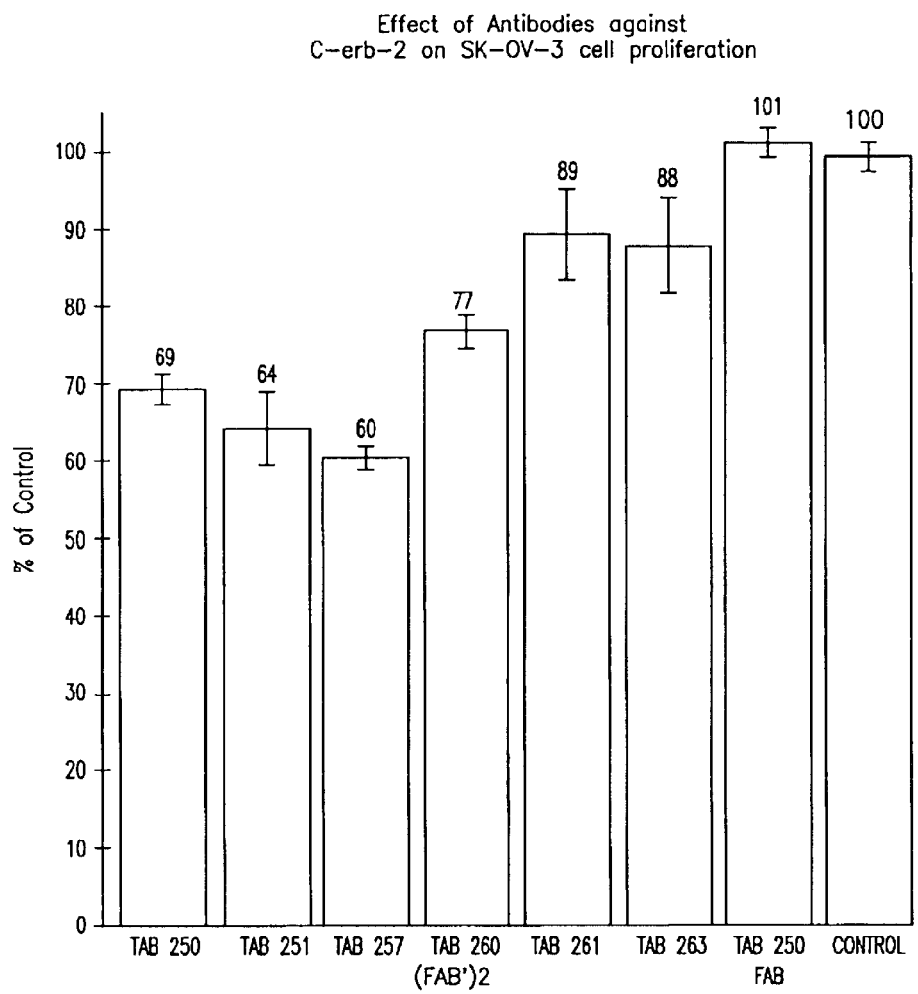

FIG. 20 shows the effects of anti-c-erbB-2 antibodies (TAbs 250, 251, 257, 261, 263, and fragments of TAb 250 [(Fab')$_2$, Fab], on the proliferation of SKOV3 cells.

DETAILED DESCRIPTION

This invention relates to compositions and methods for impeding the growth of tumor cells and for killing such cells. Combinations of anti-neoplastic drugs and ligand-mimicking agents specific to tumor cells are described which have a synergistic effect in inhibiting tumor cell growth in vitro and in vivo. Of particular importance is the discovery of the synergistic benefit of this newly-described combination.

The synergistic drug combination of the present invention comprises at least two components, an anti-neoplastic drug or agent, as defined below, and a molecule that is characterized here as a ligand-mimicking agent reactive with the c-erbB-2 protein associated with tumor cells. The second component of the combination may be characterized in several ways which will become more apparent from the description which follows.

The anti-neoplastic drugs or agents contemplated for use in this invention are those agents which are known as chemotherapeutic agents toxic to tumor cells, preferably those which are alkylating agents. Chemotherapeutic agents include alkylating agents, antimetabolites, natural products, hormones and antagonists and other miscellaneous agents. Examples of each of these agents are as follows:

CHEMOTHERAPEUTIC AGENTS
USEFUL IN NEOPLASTIC DISEASE

| CLASS | TYPE OF AGENT | GENERIC NAMES OF SPECIFIC AGENTS (OTHER NAMES) |
|---|---|---|
| Alkylating Agents | Nitrogen Mustards | Mechlorethamine (HN$_2$) Cyclophosphamide Melphalan (L-sarcolysin) Uracil mustard Chlorambucil |
| | Alkyl Sulfonates | Busulfan |
| | Nitrosoureas | Carmustine (BCNU) Lomustine (CCNU) Semustine (methyl-CCNU) Streptozocin (streptozotocin) |
| | Triazenes | Dacarbazine (DTIC; dimethyltriazen-oimidazolecarbox-amide) |
| | Platinum Coordination Complexes | Cisplatin (cis-DDP) Carboplatin Tetraplatin Ipraplatin |
| | Ethylenimine | |
| Antimetabolites | Folic Acid Analogs | Methotrexate (amethopterin) |
| | pyrimidine Analogs | Fluorouracil (5-fluorouracil; 5-FU) Cytarabine (cytosine arabinoside) |
| | Purine Analogs | Mercaptopurine (6-mercaptopurine; 6-MP) Thioguanine (6-thioguanine; TG) |
| Natural products | Vinca Alkaloids | Vinblastine (VLB) Vincristine Vindesine |
| | Epipodophyllo-toxins | Etoposide Teniposide |
| | Antibiotics | Dactinomycin (actinomycin D) Daunorubicin |

CHEMOTHERAPEUTIC AGENTS
USEFUL IN NEOPLASTIC DISEASE
-continued

| CLASS | TYPE OF AGENT | GENERIC NAMES OF SPECIFIC AGENTS (OTHER NAMES) |
|---|---|---|
| | | (daunomycin; rubidomycin) Doxorubicin Bleomycin Plicamycin (mithramycin) Mitomycin (mitomycin C) |
| Miscellaneous Agents | Enzymes Substituted Urea | L-Asparaginase Hydroxyurea |
| | Methyl Hydrazine Derivative Adrenocortical Suppressant | Procarbazine (N-methylhydrazine, MIH) Mitotane (o,p'-DDD) Aminoglutethimide |
| Hormones and Antagonists | Adrenocorti-costeroids | Prednisone |
| | Progestins | Hydroxyprogester-one caproate Medroxyprogester-one acetate Megestrol acetate |
| | Estrogens | Diethylstilbestrol Ethinyl estradiol |
| | Antiestrogen | Tamoxifen |
| | Androgens | Testosterone propionate Fluoxymesterone |

For alkylating agents, the function of the cancer cell is disrupted because the drugs alkylate the DNA, RNA, or enzymes of the cell. Alkylating agents or compounds for the purposes here encompass heavy metal compounds like the platinum coordination compounds, such as cisplatin, carboplatin, tetraplatin, ipraplatin, and the like; nitrogen mustard compounds, such as phenylalanine mustard (melphalan), and the like; ethylenimines; alkyl sulfonates; nitrosoureas; triazenes; and the like. Most preferred alkylating compounds include the platinum compounds and nitrogen mustard compounds. (See *Medical Oncology. Basic Principles and Clinical Management of Cancer* (1985) Calabresi, P., Schein P. S., Rosenberg, S. A. (eds.), Macmillan Publishing Co., pages 292–307.)

Platinum coordination complexes or compounds exist in two arrangements: platinum (II) dsp$^2$, which have a square planar arrangement and platinum (IV) d$^2$sp$^3$, which have an octahedral arrangement. In conventional therapy, the compounds are usually administered parenterally with about 0.5 milligrams to about 10 milligrams of compound per milliliter (mg/ml) of a suitable pharmaceutical carrier. Generally, a dosage level of from about 20 to about 200 milligrams per kilogram (mg/kg) of body weight per day is used, depending upon the particular compound employed. One of the most widely prescribed platinum drugs for cancer treatment is cisplatin (cis-diamminedichloroplatinum) described in U.S. Pat. No. 4,177,263 and which is hereby incorporated by reference. Another platinum drug useful in the treatment of ovarian carcinoma is carboplatin (cis-diammine-1,1-cyclobutane dicarboxylate platinum) described in U.S. Pat. Nos. 4,140,707 and 4,657,927 and which are hereby incorporated by reference. Carboplatin, when used alone in the treatment of ovarian carcinoma, is administered to a woman by intravenous infusion for about 15–30 minutes every four weeks at a dosage of about 360 milligrams per square meter (mg/m$^2$). Other platinum compounds that can be used are 1,2-diaminocyclohexane (DAC) platinum compounds, such as tetraplatin. Guidelines for administering the other anti-neoplastic agents are known in the art and may be found in *Goodman* and *Gilman's The Pharmacological Basis of Therapeutics* 1240–1306 (Gilman, et al. eds. 7th ed. 1985); and *Harrison's Principles of Internal Medicine* 1587–99, 1612–25 (Wilson, et al. eds. 12th ed. 1991), which are both incorporated by reference herein.

Melphalan is a nitrogen mustard derivative of L-phenylalanine, known as 4-[bis(2-chloroethyl)amino] L-phenylalanine, which is administered orally at 0.25 mg/kg or intravenously at 0.1 to 0.15 mg/kg daily. It causes marked bone marrow depression, but is used in multiple myeloma and epithelial ovarian carcinoma.

While anti-neoplastic agents are somewhat effective in the treatment of cancer, they are unable to specifically target the tumor cell without affecting the surrounding normal cells, so higher dosages are disadvantageous. In addition, high dosages of alkylating agents for example are nephrotoxic and neurotoxic, and depress the bone marrow; therefore, an effective, but lower, dosage of these compounds is highly desirable. Though typical recommended dosages of the anti-neoplastic drugs may be used in the synergistic drug combinations and treatments described here, lower dosages are preferable and possible due to the synergistic effect. Dosages as much as 10 to 100 times lower may be used when platinum compounds or other alkylating compounds are combined with ligand-mimicking agents. For example, using cisplatin alone in conventioal therapies requires a serum level of about 1 microgram per milliliter ($\mu$g/ml), which is about a dose level of 50 micrograms per kilogram ($\mu$g/kg) of body weight.

The second component of the synergistic combination is a "ligand-mimicking agent reactive with the c-erbB-2 protein associated with tumor cells." The ligand-mimicking agent specific to tumor cells is a molecule that acts as a ligand or partial agonist to the c-erbB-2 protein receptor on tumor cells. Though the term "ligand mimicking" is used, a purified form of an actual appropriate isolated ligand or a portion or fragment thereof, is intended to be covered by this term. The ligand for the c-erbB-2 protein may be identified and extracted from appropriate cells or cell culture supernatants and isolated by using c-erbB-2 protein in detection assays. Alternatively, the ligand mimicking agent may also be produced by peptide synthesis or by recombinant means. An isolated ligand may be a component of an isolated molecule, such as an oligosaccharide, a polypeptide fragment, or a glycoconjugate. An example of a method for synthesizing peptide ligand-like substrates is found in Pike, *Meth. in Enzymolog.*, 146:353 (1987), incorporated by reference herein.

The c-erbB-2 protein (also referred to as c-erbB-2 protein receptor) is a 185 Kd glycoprotein having tyrosine kinase activity and is related to, but distinct from, the epidermal growth factor receptor (EGFR). Like the EGFR protein, the c-erbB-2 protein has an extracellular domain that includes two cysteine-rich repeat clusters, a transmembrane domain and an intracellular kinase domain. In addition, the amino acid sequence of the c-erbB-2 protein as well as the nucleotide sequence has been described by Coussens, et al. *Science*, 230:1132 (1985), incorporated by reference herein. The c-erbB-2 protein is encoded by the c-erbB-2 oncogene described in 1985 by three different research groups: Semba, et al *Proc. Natl. Acad. Sci. USA*, 82:6497 (designating the gene as c-erbB-2); Coussens et al, supra, (designating the gene as HER-2); and King, et al., *Science*, 229:1132 (designating the gene as v-erbB related). Thus, the c-erbB-2 gene and its protein are well-known and described in the art. Detection for the presence of the c-erbB-2 protein may be accomplished by well-known immunoassays employing antibodies specific to the c-erbB-2 protein. Such antibodies are commercially available from Chemicon International, Inc., Temecula Calif. or may be developed by standard antibody procedures. It is intended herein that the c-erbB-2 protein definition will also include those proteins occurring in other host systems that are immunologically related to the human c-erbB-2 protein. For example, a related rat gene (designated neu) has been reported in Schecter, et al., *Science*, 229:976 (1985).

Of particular interest as a ligand-mimicking agent is a molecule that binds tumor cells and induces an increase in the phosphorylation of the c-erbB-2 protein when placed in contact with tumor cells expressing the c-erbB-2 protein. A molecule that induces an increase in the phosphorylation of c-erbB-2 protein is one that causes a detectable increase in the incorporation of phosphate into the protein over that which occurs in the absence of the molecule. Typically this detectable increase will be a two-fold or greater increase in phosphorylation, preferably greater than a three-fold increase over controls. Phosphorylation may be measured by those methods known in the art for detecting phosphorylation of receptors. See, for example Cooper, et al., *Methods in Enzymolog.*, 99:387–402 (1983); Antoniades and Pantazis, *Methods in Enzymolog.*, 147:36–40 (1987); and Lesniak, et al., *Methods in Enzymolog.*, 150:717–723 (1987), which are all incorporated by reference herein. See also Example 8D below.

Typically, phosphorylation can be measured by in vivo, phosphorylation of intact cells (Lesniak, supra) or by an in vitro autophosphorylation reaction (Antonaides, supra). For measuring in vivo phosphorylation, for example, assays may be conducted where cells bearing the receptor are placed into contact with radioactive labelled phosphate. To detect phosphorylation of the c-erbB-2 protein receptor in the in vivo assay, it is advantageous to incubate the test cells for about 12 to about 18 hours, with the labeled phosphate. The cells are divided into two or more batches, where some are exposed to the molecule expected to increase the phosphorylation of the receptor and some are separated out as controls. The aliquots are subsequently immunoprecipitated, the receptor is recognized and an increase in phosphorylation is detected when there is a two-fold or greater increase in the background of the aliquot exposed to the test molecule over the control aliquots.

To measure In vitro autophosphorylation, cells or cell extracts are incubated in the presence or absence of the ligand-mimicking agent. Following immunoprecipitation with an anti-c-erbB-2 antibody, the immune complex may be incubated with $\gamma^{32}$P-ATP and analyzed by SDS-PAGE autoradiography.

A molecule that binds tumor cells for the purposes of the inventions herein is one that is reactive with the c-erbB-2 protein. By "reactive" it is meant that the molecule binds the c-erbB-2 protein as measured or determined by standard ligand-receptor binding assays, for example, competitive binding assays or saturation assays or standard immunoassays such as ELISA or RIA.

In competition assays the ability of a molecule to bind a receptor is determined by detecting the ability of the molecule to competitively inhibit binding of any compound known to bind either the receptor or the ligand. Numerous types of competitive assays are known and are discussed herein. Alternatively, assays that measure binding of a test compound in the absence of an inhibitor may also be used. For instance, the ability of a molecule or other compound to bind the receptor can be detected by labelling the molecule of interest directly or it may be unlabelled and detected indirectly using various sandwich assay formats.

Other assay formats may involve the detection of the presence or absence of various physiological or chemical changes in the ligand-mimicking agents that result from the interaction, such as down modulation, internalization or an increase in phosphorylation as described here. See also, *Receptor-Effector Coupling—A Practical Approach*, ed. Hulme, IRL Press, Oxford (1990). Preferably, the dissociation constant ($K_D=1/K$, where K is the affinity constant) of the ligand-mimicking agent is <100 nM, most preferably <1 nM. $K_D=[R-L]/[R][L]$ where [R], [L], and [R-L] are the concentrations at equilibrium of the receptor (R), ligand (L) and receptor-ligand complex (R-L), respectively. Typically, the binding interactions between ligand and receptor include reversible noncovalent associations such as electrostatic attraction, Van der Waals forces and hydrogen bonds.

The ligand-mimicking agent reactive with tumor cells, which is the second component of the synergistic combination, may alternatively be characterized as a molecule that causes down modulation of the c-erbB-2 protein. Down modulation of the c-erbB-2 protein is determined by a detectable decrease in the presence on the tumor cells of the c-erbB-2 receptor. Down modulation is detected by a decrease in the ability of antibodies or other specific binding moieties to bind to or recognize the c-erbB-2 receptor protein on the tumor cells. For example, down modulation can be determined by incubating tumor cells bearing the c-erbB-2 protein receptor with the ligand-mimicking agent of interest, washing the cell, then contacting the cells with labeled (preferably radiolabelled) antibodies specific for the c-erbB-2 protein, and comparing the extent of binding of the labelled anti-c-erbB-2 antibodies to the cells exposed to the ligand-mimicking agent to the extent of binding of the antibodies to control cells (i.e., not exposed to the ligand-mimicking agent). See also Example 8A. Preferably for these assays, the cells are directly subjected to the labeled anti-c-erbB-2 antibodies after washing.

The down modulation observed will be dose dependent, i.e., the extent of down modulation increases with the amount of ligand-mimicking agent exposed to the protein. Preferably, a ligand-mimicking agent that causes a decrease in 90% or greater of binding of the treated cells versus control cells to anti-c-erbB-2 antibodies is desirable. A preferred ligand-mimicking agent, TAb 250, for example, causes down modulation which is reversed over time by growth of the cells in media free of TAb 250.

Numerous types of binding assays such as competitive binding assays are known (see, e.g., U.S. Pat. Nos. 3,376, 110, 4,016,043, and Harlow and Lane, *Antibodies: A Laboratory Manual*, Cold Spring Harbor Publications, N.Y. (1988), which are incorporated herein by reference). Assays for measuring binding of a test compound to one component alone rather than using a competition assay are also available. For instance, immunoglobulins can be used to identify the presence of the c-erbB-2 protein. Standard procedures for monoclonal antibody assays, such as ELISA, may be used (see, Harlow and Lane, supra). For a review of various signal producing systems which may be used, see, U.S. Pat. No. 4,391,904, which is incorporated herein by reference.

The ligand-mimicking agent may be alternatively characterized as a molecule that binds tumor cells expressing c-erbB-2 protein and causes internalization of c-erbB-2 protein receptor when placed in contact with such tumor cells. "Internalization" occurs when the receptor becomes sequestered in the cytoplasm of the cells. Once internalized, the receptor may be degraded in the cell lysosomes or may be recycled to the cell surface. Internalization is determined by a decrease in the availability of the receptor to bind ligand, which may be determined by competitive binding assays. Also, once the c-erbB-2 protein is internalized, the ligand mimicking agent can not be stripped from the cells by acid washing. A method for determining internalization of a ligand-receptor complex is also described in Haigler, et al., *J. Biol. Chem.*, 255:1239–1241 (1980), incorporated by reference herein, and in Example 8B. Internalization of the c-erbB-2 protein caused by the ligand mimicking agent is typically seen within fifteen minutes after binding.

Preferred ligand-mimicking agents specific to tumor cells are those which provide specificity to the tumor cells. Particularly suited for this purpose are monoclonal antibodies, or reactive fragments thereof, to the c-erbB-2 protein. For example, the preferred ligand-mimicking agent is monoclonal antibody TAb250 produced by hybridoma 20.3, which has been deposited with The American Type Culture Collection in 10801 University Blvd, Manassas, Va. 20110-2209 on Jan. 16, 1991, designated No. HB 10646. Reactive fragments of TAb 250 may be used and antibodies substantially similar to TAb 250 are also preferred. Antibodies that are substantially similar to TAb 250 are those antibodies which inhibit the binding of TAb 250 in competitive inhibition assays, those that phosphorylate the c-erbB-2 protein and those that cause down modulation of the c-erbB-2 protein.

Although a ligand-mimicking antibody can be raised to the entire expressed c-erbB-2 gene product or portions of the product, it is preferable for the ligand-mimicking agent to target the extracellular (ectodomain) portion of the c-erbB-2 oncogene. Bernards, et al. *Proc. Nat'l. Acad. Sci.* (USA) (1987), 84:6854 described the expression of the external domain, the transmembrane anchor domain and about 50 amino acids of the intracellular domain of the neu oncogene in a vaccinia virus.

The antigen can be prepared by peptide synthesis or recombinant DNA means, depending upon the length of the amino acid sequences desired for the antigen. Transfected NIH3T3 cells or SKBR3 cells as well as other cells which overexpress the c-erbB-2 protein, may also be used as the antigen, either through the use of the whole cell or cell membrane.

In all cases, murine, human or chimeric antibodies may be used. The antibodies can be prepared in a variety of ways known in the art, depending upon whether monoclonal or polyclonal antibodies are desired. For polyclonal antibodies, a vertebrate, typically a domestic animal, is hyperimmunized with the antigen and blood from the vertebrate is collected shortly after repeat immunizations and the gamma globulin is isolated. Suitable methods for preparing polyclonal antibodies are described in the *Handbook of Experimental Immunology* (1978) 3d ed., Weir (ed.), Blackwell Scientific Publications.

For monoclonal antibodies, a small animal, typically a rat or mouse, is hyperimmunized with antigen, the spleen removed and the lymphocytes fused with myeloma cells in the presence of a suitable fusion promoter. The resulting hybrid cells or hybridomas are screened to isolate individual clones, each of which secrete a single antibody species to the antigen. The individual antibody species are each the product of a single B cell generated in response to a specific antigenic site recognized on the antigen or immunogenic substance. The process for obtaining monoclonal antibodies is described by Kohler and Milstein, *Nature* (1975), 256:495. See also Harlow and Lane, supra. The peptides or antigens used to generate the antibodies, depending upon their own immunogenicity, may be used directly in the immunization procedure as immunogenic components associated with living or fixed cells or they may be bound to a suitable carrier protein, such as keyhole limpet hemocyanin (KLH), human or bovine serum albumin (HSA or BSA), and the like. Use of the antigen with a carrier protein is preferred.

To identify antibodies, with the desired specificity, a number of well-defined techniques, such as their ability to stain tumor cells via histochemical means, to react with intact tumor cells on a Fluorescence-activated cell sorter (FACS), or to react with the purified oncogene protein in either a radioimmunoprecipitation (RIP) assay or in a Western blot assay. There will be more than one relevant epitope on the c-erbB-2 protein for generation of useful antibodies.

A cocktail of ligand-mimicking agents can also be used in this combination to further enhance the effects of the synergistic drug combination. Once the agents have been selected, their effectiveness can be measured by the level at which they affect the growth of tumor cells and the extent they promote synergism in combination with the anti-neoplastic drug.

The use of high concentrations of mouse antibodies (or other animal antibodies) in humans does have certain limitations. There are instances of anti-framework or anti-idiotype antibodies being generated over the course of long-term therapy. Therefore, chimeric antibodies may also be used in the combination of this invention, which can minimize an antimurine response. Chimeric antibodies are usually combinations of portions of human and murine antibodies with the variable region of the murine line combined with the invariant or constant region of the human line. An example of a successful human/murine chimeric antibody is one for carcinoembryonic (CEA) antigen described by Beidler, et al. *J. of Immunology* (1988), 141:4053. Other methods for constructing chimeric antibodies and binding fragments are described in Brown et al., *Cancer Research*, 47:3577–3583 (1987); Kameyama et al., *FEB* 2:301–306 (1989); Orlandi et al., *Proc. Nat'l Acad. Sci., USA*, 86:3833–3837 (1989); Beidler et al., *J. Immun.*, 141:4053 (1986); Sahagan et al., *J. Immunol.*, 3:1066 (1986); Bird et al.,*Science,* 242:123 (1988); Morrison et al., *Clin. Chem.*, 34:1668–1675 (1988); Better et al., *Science*, 240:1041 (1988) and Morrison and Oi, *Advances in Immunology*, 44:55 (1989) all of which are incorporated by reference herein.

As used herein, the term "antibody" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. The ligand-mimicking agents may exist in a variety of forms besides antibodies, including for example, Fv, Fab, and $F(ab')_2$, as well as in single chains (e.g., Huston et al., *Proc. Nat. Acad. Sci. U.S.A.*, 855879–5883 (1988) and Bird et al., *Science,* 242:423–426 (1988), which are incorporated herein by reference). (See, generally, Hood et al., *Immunology*, 2nd ed., Benjamin, N.Y. (1984), and Hunkapiller and Hood, *Nature*, 323:15–16 (1986), which are incorporated herein by reference.) The $F(ab')_2$ fragment may be obtained from the antibody by digestion with pepsin at pH 3.0–3.5 using standard methods. The fragment retains both of the antibody combining sites attached by the hinge disulfide. The Fab fragment is obtained by reduction of the disulfide in the hinge region of the whole antibody or of the $F(ab')_2$ fragment usually with papain. Therefore, two Fab fragments are obtained from one $F(ab')_2$ fragment.

The synergistic combinations of this invention produce cytotoxicity, which may kill tumor cells. Though typical recommended dosages of the anti-neoplastic drugs may be used in the synergistic drug combinations and treatments described here, lower dosages are preferable and possible due to the synergistic effect. Dosages as much as to 100 times lower can be used when the drug is combined with the ligand-mimicking agent.

Tumors or cancers to be treated with the combinations of this invention are any tumors which express, or are suspected of expressing, the c-erbB-2 oncogene protein or have amplification of the c-erbB-2 gene. These tumors include, for example: breast, ovarian, bladder, prostatic, prostate, stomach, and thyroid cancers. Breast and ovarian cancers are most effectively to be treated using the combinations herein. The c-erbB-2 protein is reported to be expressed in: solid tumors by, for example, Gutman et al., *Int. J. Cancer,* 44:802–805 (1989); in human adenocarcinomas by Yokota et al., *The Lancet,* Apr. 5, 1986, p.765; in gastric and esophageal carcinomas by Houldsworth et al., *Cancer Res.,* 50:6417–22 (1990); in neoplastic cervix, vulva and vagina by Berchuck et al., *Obstetrics. Gynecol. Surv.,* 76:381 (1990); in renal cell carcinoma by Weidner et al., *Cancer Res.,* 50:4504 (1990); in lung adenocarcinomas by Kern et al., *Cancer Res.,* 50:5184–5191 (1990) and Schneider et al., *Cancer Res.,* 49:4968–4971 (1989); in gastric cancer by Fukushige et al., *Mol. and Cell. Biol.,* 6:955–958 (1986), Park et al., *Cancer Res.,* 49:6605 (1989); in breast and ovarian cancer by Slamon et al. *Science,* 244:707 (1989); by Berchuck et al., *Cancer Res.,* 50:4087 (1990); by Van de Vijver et al., *Mol. Cell Biol.,* 7:2019–2023 (1987), by Varley et al., *Oncogene,* 1:423–430 (1987), Bacus et al., *Am. J. Path.,* 137:103 (1990) all of which are incorporated by reference herein.

The synergistic combination of this invention can be administered concurrently or sequentially, with either component being administered first. The combination can be used in either pre- or post-operative treatment of cancer or both.

The compositions herein are preferably administered to human patients via oral, intravenous or parenteral administrations and other systemic forms. The pharmaceutical formulations or compositions of this invention may be in the dosage form of solid, semi-solid, or liquid such as, e.g., tablets, pills, powders, capsules, gels, ointments, liquids, suspensions, aerosols or the like. Preferably the compositions are administered in unit dosage forms suitable for single administration of precise dosage amounts. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier will be those amounts which are effective to obtain a pharmaceutically acceptable formulation in terms of solubility of components, or biological activity, etc. Generally a dosage level of from 1–500 mg/m² of body surface area may be used systemically for the ligand-mimicking agent, to be adjusted as needed for the particular agent used and with the anti-neoplastic agent taken into consideration.

The expression "synergistic" or "synergistically effective amounts" of the ligand-mimicking agent and the anti-neoplastic drug or agent refers to amounts of each component of the combination which together are effective in producing more than an additive effect of the components alone. Therefore, the combination's effect is greater than the sum of the effects of the two components.

The ligand-mimicking agent and the anti-neoplastic agent are not conjugated. By "not conjugated" it is meant that the two components are separate and not covalently linked.

The tumor cells that one wishes to kill or control the growth of are referred to as "target tumor cells." "Test tumor cell" are any tumor cells in vitro that express the c-erbB-2 protein.

The following examples are offered by way of illustration, not by way of limitation.

EXAMPLES

The following examples make reference to the terms listed below and defined:

| | |
|---|---|
| ATCC | American Type Culture Collection |
| BSA | bovine serum albumin |
| CHO | Chinese hamster ovary |
| $CO_2$ | Carbon dioxide |
| DMEM | Dulbecco's modified Eagle medium |
| EDTA | ethylenediaminetetraacetic acid |
| EGFr | Epidermal Growth Factor receptor |
| EGTA | ethylene glycol-bis (α-aminoethyl ether)-N, N, N', N'-tetraacetic acid |
| ELISA | enzyme-linked immunosorbent assay |
| FACS | fluorescence - activated cell sorter |
| FBS | fetal bovine serum |
| FITC | fluorescein isothiocyanate |
| HAT | hypoxanthine aminopterine thymidine |
| HBSS | Hank's balanced salt solution |
| HCl | hydrochloric acid |
| HEPES | 4-(2-hydroxyethyl)-1-piperazineethanesulfonic acid |
| HPLC | high pressure liquid chromatography |
| IRMA | immunoradiometric assay |
| MAb | monoclonal antibody |
| MEM | minimal essential medium |
| MTT | 3-(4,5-dimethylthiazolyl-2-yl)-2,5-diphenyl tetrazolium bromide |
| PBS | phosphate-buffered saline |
| PEG | polyethylene glycol |
| PMSF | phenylmethylsulfonyl fluoride |
| PNPP | para-nitrophenyl phosphate |
| RIA | radioimmunoassay |
| SDS | sodium dodecyl sulfate |
| SDS-PAGE | sodium dodecyl sulfate-polyacrylamide gel electrophoresis |
| TCA | trichloroacetic acid |
| TRIS | tris (hydroxymethyl) aminomethane or 2-amino-2-hydroxymethyl-1,3-propanediol |

-continued

| | |
|---|---|
| Cell Lines | |
| SKBR3 | Human breast cancer cell line expressing the c-erbB-2 protein, which originated as a human metastatic pleural effusion obtained from the ATCC, catalog #HTB30. |
| SKOV3 | Human ovarian cancer cell line expressing the c-erbB-2 protein, which originated as a metastatic ascitic effusion obtained from the ATCC, catalog #HTB77. |
| MDA361 | Human breast cancer cell line expressing the c-erbB-2 protein, which originated as a metastatic tumor to the brain obtained from the ATCC, catalog #HTB27. |
| MDA466 | Breast cancer cell line which originated as a metastatic pleural effusion and contains amplified EGFr obtained from the ATCC, catalog #HTB132. |
| HBL100 | Breast cell line derived from human milk obtained from the ATCC, catalog #HTB124. |
| NIH3T3 | Murine fibroblast cell line obtained from S. Aaronson, National Institutes of Health. |
| NIH3T3$_t$ | Murine fibroblast cell line transfected with the human c-erbB-2 gene and expressing high levels of c-erbB-2 protein on the cell membrane obtained from S. Aaronson, National Institutes of Health. |
| Growth Media | |
| SKBR3, MDA46B | Cells were cultured in Minimal Essential Medium (MEM), (Gibco Biologicals Inc., New York), 10% heat inactivated fetal bovine serum, 0.29 mg/ml L-glutamine. |
| SKOV3 | Cells were cultured in Iscove's Modified Dulbecco's Medium (IMDM), 10% heat inactivated fetal bovine serum, 0.29 mg/ml L-glutamine. |
| MDA361 | Cells were cultured in RPMI 1640 (Gibco), 10% heat inactivated fetal bovine serum, 10 μg/ml bovine pancreatic insulin, 0.29 mg/ml L-glutamine. |
| HBL100 | Cells were cultured in McCoy's 5A medium (Gibco), 10% heat inactivated fetal bovine serum, 0.29 mg/ml L-glutamine. |
| Reagents | |
| Cisplatin (CDDP) | cis-diamminedichloroplatinum. "Platinol" (cisplatin for injection). Produced by Bristol Laboratories, Oncology Products, Evansville, IN 47721. It was reconstituted with sterile water to yield 1 mg/ml and either used immediately or stored frozen. Dilutians were made in PBS immediately prior to use. |
| Carboplatin | cis-diammine-1,1-cyclobutane dicarboxylate platinum. "Paraplatin" (carboplatin for injection). Produced by Bristol Laboratories, Oncology Products, Evansville, IN 47721. One hundred fifty mg per vial was reconstituted with 15 ml of sterile water to yield 10 mg/ml solution which was either used |

-continued

| | |
|---|---|
| Melphalan | immediately or aliquoted and frozen, and diluted further in PBS immediately prior to use. 4-[bis(2-chloroethyl)amino]L-phenylalanine. Obtained from Sigma Chemical Co., St. Louis, MO 63178. Product # M2011. One mg was reconstituted in sterile water. The solution sat for 1 hour at room temperature to dissolve and was diluted further in PBS immediately prior to use. |
| MTT | Obtained from Sigma Chemical Co., St. Louis, MO. Product # M2128. MTT was reconstructed at 5 mg/ml in PBS, warmed to 37° C. for 30–60 minutes, then filtered through a 0.22 μm filter. Solution is light sensitive and can be stored at 4° C. for up to one month. |

Example 1
Preparation of c-erbB-2 Monoclonal Antibodies

Balb/c mice were immunized intraperitoneally and subcutaneously with $2 \times 10^6 – 1 \times 10^7$ NIH3T3 cells transfected with the human c-erbB-2 oncogene, NIH3T3$_t$, (kindly provided by Dr. S. Aaronson, NIH) (*Science*, 237:178–182) or with a similar number of SKBR3 cells emulsified 1:1 volume/volume in complete Freund's adjuvant. Sera was collected every two weeks and tested for reactivity in an ELISA assay (described below) against formalin fixed NIH3T3 or fixed NIH3T3$_t$ cells. Animals with positive titers were boosted intraperitoneally or intravenously with cells in PBS, and animals were sacrificed 4 days later for fusion. Spleen cells were fused with P3-X63Ag8.653 myeloma cells at a ratio of 1:1 to 7.5:1 with PEG 4000 as described by the procedure of Kohler and Milstein (*Nature*, 256:495–497). Fused cells were gently washed and plated in 96-well plates at $1–4 \times 10^6$ cells/ml in RPMI 1640 medium. Wells were fed with HAT medium 24 hours after the fusion and then every 3 days for 2–3 weeks. When colony formation was visible, after 10–14 days, the supernatants were tested for reactivity in the ELISA assay. Prospective clones demonstrating good growth were expanded into 24-well plates and rescreened 7–10 days later. Positive wells were then assayed for external domain reactivity against live NIH3T3 and NIH3T3$_t$ cells by flow sorting analysis. Clones which were positive both by ELISA assay and flow sorting analysis were recloned either by limiting dilution or by single cell deposition using a flow cytometer. Cells were diluted and deposited into 96-well plates in the presence or absence of spleen feeder cells. Wells demonstrating growth were retested by ELISA and recloned an additional one to three times. Supernatants from hybridoma clones were tested for isotype and subisotype, reactivity to surface expressed p185 protein on NIH3T3$_t$ cells by flow sorting analysis, and immunoprecipitation of a labeled p185 protein from transfected cells. Positive hybridomas were grown in tissue and injected into pristane-primed Balb/c mice, Balb/c nude mice or IRCF$_1$ mice for ascites production. Monoclonal antibodies were purified from ascites fluid by HPLC using a Bakerbond ABx column. Purified monoclonal antibodies (referred to by TAb number) were dialyzed against PBS and stored at −20° C. All purified antibodies were tested for isotype, subisotype, and contaminating isotypes by radial immunodiffusion. Cell surface staining of p185 expressing cell lines was detected and quantified by flow sorting analysis, ELISA assay against transfected and untransfected NIH3T3 cells, and radioimmunoprecipitation of p185 from labeled c-erbB-2 expressing cell lines. The antibodies do not cross-react with the closely related EGF-receptor protein as shown by the failure to precipitate a radiolabeled 170 Kd protein from radiolabeled A-431 cells, and they have been analyzed by SDS-PAGE and gel densitometry (all purified proteins are >90% immunoglobulin). A summary of the MAbs developed and the reactivity of these MAbs is outlined in Table 1.

TABLE 1

Characteristics of MAbs Recognizing the External Domain of c-erbB-2

| TAb | Immunogen | FACS[1] Binding | ELISA[2] Titer, ng/ml | Subisotype | p185 | p170 | External Domain | Western[3] Blot |
|---|---|---|---|---|---|---|---|---|
| 250 | NIH3T3$_t$ | + | 20 | IgG$_1$ | + | − | + | − |
| 251 | NIH3T3$_t$ | + | 1 | IgG$_1$ | + | − | + | − |
| 252 | NIH3T3$_t$ | + | 20 | IgG$_1$ | + | − | + | − |
| 253 | NIH3T3$_t$ | + | 47 | IgG$_1$ | + | − | + | − |
| 254 | NIH3T3$_t$ | + | 10 | IgG$_1$ | + | − | + | − |
| 255 | NIH3T3$_t$ | + | 16 | IgG$_1$ | + | − | +/− | − |
| 256 | NIH3T3$_t$ | + | 25 | IgG$_1$ | + | − | + | − |
| 257 | NIH3T3$_t$ | + | 11 | IgG$_1$ | + | − | + | − |
| 258 | NIH3T3$_t$ | + | 4 | IgG$_1$ | + | − | + | − |
| 259 | SK-BR-3 | + | 20 | IgG$_1$ | + | − | + | − |
| 260 | NIH3T3$_t$ | + | 10 | IgG$_{2a}$ | + | − | + | − |
| 261 | NIH3T3$_t$ | + | 10 | IgG$_{2b}$ | + | − | +/− | − |
| 262 | NIH3T3$_t$ | + | 27 | IgG$_1$ | + | − | + | − |
| 263 | NIH3T3$_t$ | + | 100 | IgG$_{2b}$ | + | − | + | − |
| 264 | NIH3T3$_t$ | + | 41 | IgG$_1$ | + | − | + | − |
| 265 | NIH3T3$_t$ | + | 51 | IgG$_1$ | + | − | + | − |
| 266 | NIH3T3$_t$ | + | 20 | IgG$_1$ | + | − | + | − |
| 267 | NIH3T3$_t$ | + | 10 | IgG$_1$ | + | − | + | − |
| 268 | NIH3T3$_t$ | + | ND | ND | + | − | + | − |

TABLE 1-continued

Characteristics of MAbs Recognizing the External Domain of c-erbB-2

| TAb | Immunogen | FACS[1] Binding | ELISA[2] Titer, ng/ml | Subisotype | p185 | p170 | External Domain | Western[3] Blot |
|---|---|---|---|---|---|---|---|---|
| 269 | NIH3T3$_t$ | + | 10 | IgG$_1$ | + | – | + | – |
| 270 | NIH3T3$_t$ | + | ND | ND | + | ND | ND | – |

[1]FACS—Fluorescence Activated Cell Sorter Analysis
[2]ELISA—ELISA titer was calculated at 30% of maximal binding to NIH3T3$_t$.
[3]Western blot was carried out under reducing conditions.
ND—Not determined.

Flow Sorting Analysis

NIH3T3 and NIH3T3$_t$ cells were grown to 80% confluency in DMEM+4% FBS. Cells were harvested with Puck's Versene (Gibco), and washed twice with cold FACS buffer (HBSS without phenol red, 2% FBS, 0.2% sodium azide, 10 mM HEPES). Cells were distributed at 0.5–1.0×10$^6$ cells per 12×75 mm glass test tube (cells should be >90% viable), pelleted, and the supernatants removed. The tubes were placed on ice and 100 µl of supernatants or purified antibodies were added per tube. Each antibody or supernatant was tested against both NIH3T3 cells as well as NIH3T3$_t$ cells. The antibody was incubated with the cells on ice for 1 hour. The cells were washed twice with cold FACS buffer, and 100 µl of a FITC-conjugated goat anti-mouse secondary antibody was added. After 1 hour on ice, the cells were washed twice with FACS buffer and resuspended to 500 µl with 10% neutral buffered formalin. (The resuspended cells can be stored wrapped in foil for up to 2 days at 4° C.). The labeled cells were analyzed in a Coulter EPICS 541 flow sorter and a mean channel fluorescence determined for 5000 cells. The mean channel fluorescence reactivity to NIH3T3$_t$ cells was compared to the mean channel fluorescence reactivity to NIH3T3 cells. For antibodies reacting with the external domain portion of p185, the peaks were non-overlapping.

ELISA Assays

Polystyrene 96-well plates were pretreated for 2 hours at 37° C. with bovine collagen at 1 mg/ml in sterile PBS at 100 µl/well. NIH3T3 or NIH3T3$_t$ cells were grown to 80% confluency in DMEM+4% FBS, harvested with warm Puck's Versene, washed and plated overnight at 37° C. at 1×10$^6$ cells/ml, 100 µl/well, in the previously treated and washed collagen plates. Plates were gently washed and treated for 1 hour with 100 µl/well of 10% neutral buffered formalin. The plates were again washed with PBS, and blocked with 1% BSA in PBS for 1 hour at 37° C. Sample supernatants or antibody dilutions were then added to the coated, blocked and washed plates at 100 µl per well and the plates were incubated for 2 hours at 37° C. After another PBS wash step, 100 µl/well of a 1:500 dilution of an alkaline phosphatase-conjugated goat anti-mouse IgG Fc-specific secondary antibody was added and the plates were incubated for 1 hour at 37° C. After a final PBS wash, a BioRad substrate (PNPP+diethanolamine) was added, and after a 10–15 minute incubation at room temperature, the absorbance was measured at 405 nanometers (nm).

Example 2

MTT Assay

Figure 1:
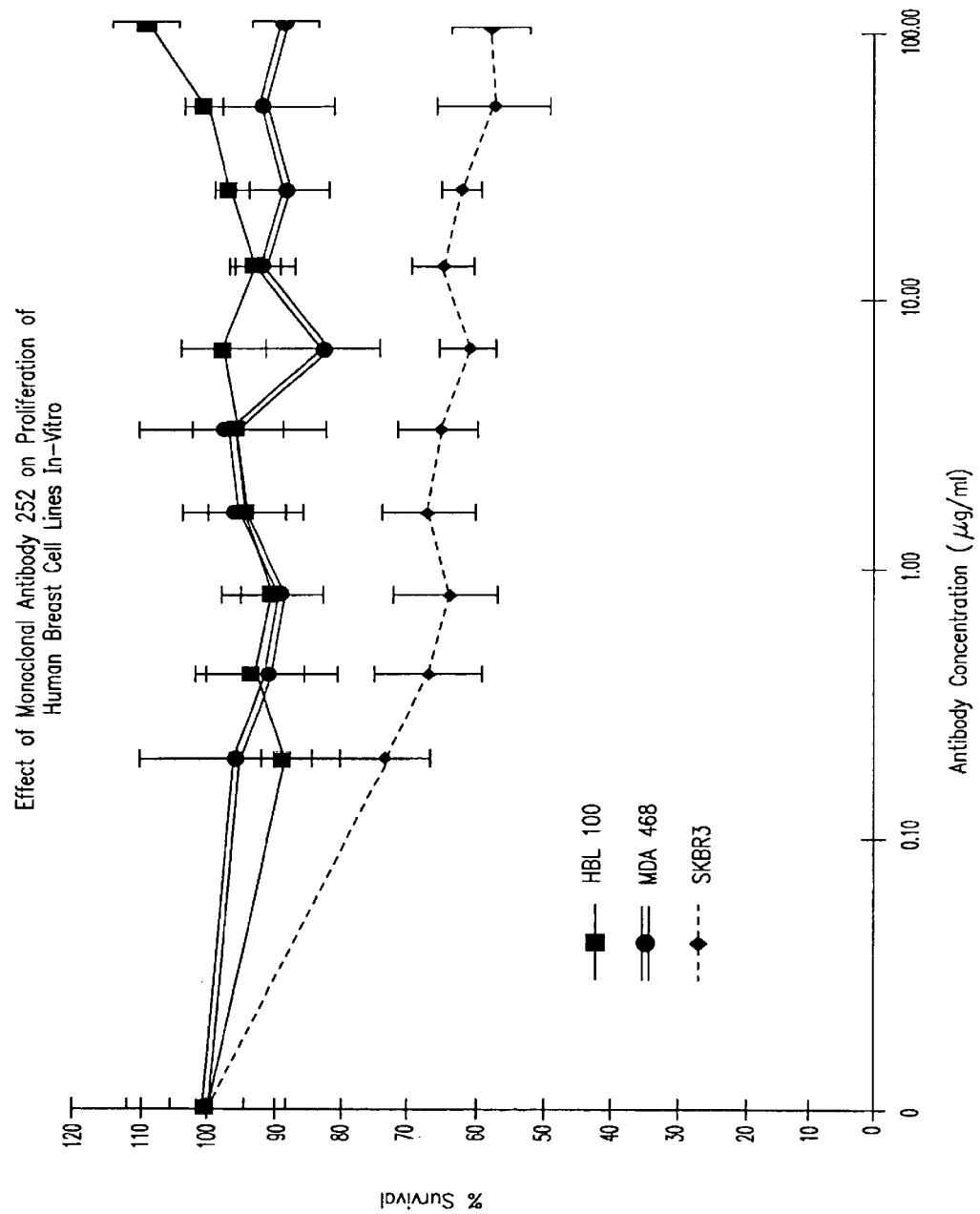
FIG. 1 shows the effects of a particular monoclonal antibody to c-erbB-2 (TAb 252) on the proliferation of three human breast cancer cell lines: HBL100, MDA468, and SKBR3. The cell line HBL100 was derived from normal breast epithelial cells, while MDA468 and SKBR3 are breast cancers which originated as human metastatic pleural effusions. However, only SKBR3 overexpresses the c-erbB-2 protein. TAb 252 inhibited the growth of the SKBR3 cells, but did not inhibit the HBL100 or MDA468 cells.

The MTT assay is generally used to assess cellular viability as a function of mitochondrial activity. The assay was used to examine effects of cisplatin with and without the c-erbB-2 monoclonal antibodies and was carried out as follows:

SKBR3 cells were seeded in 96-well microtiter plates (1×10$^4$ cells/well), and 24 hours later, dilutions of TAb 250 or a non-specific IgG1 isotype control antibody were added followed immediately by cisplatin (1 µg/ml or 3 µg/ml). Plates were incubated for an additional 72 hours. MTT was added for 4 hours and the crystals dissolved with isopropanol/0.04N HCl/0.3% SDS. Absorbance at 570 nM was determined using an ELISA reader. It was found that growth inhibition was restricted to cells expressing the c-erbB-2 protein. FIG. 1 demonstrates the response of SKBR3 cells in contrast to two other breast cell lines that do not express c-erbB-2. Neither HBL100 nor MDA468 (which overexpress EGF receptors) was inhibited by the TAb 252.

Figure 2:
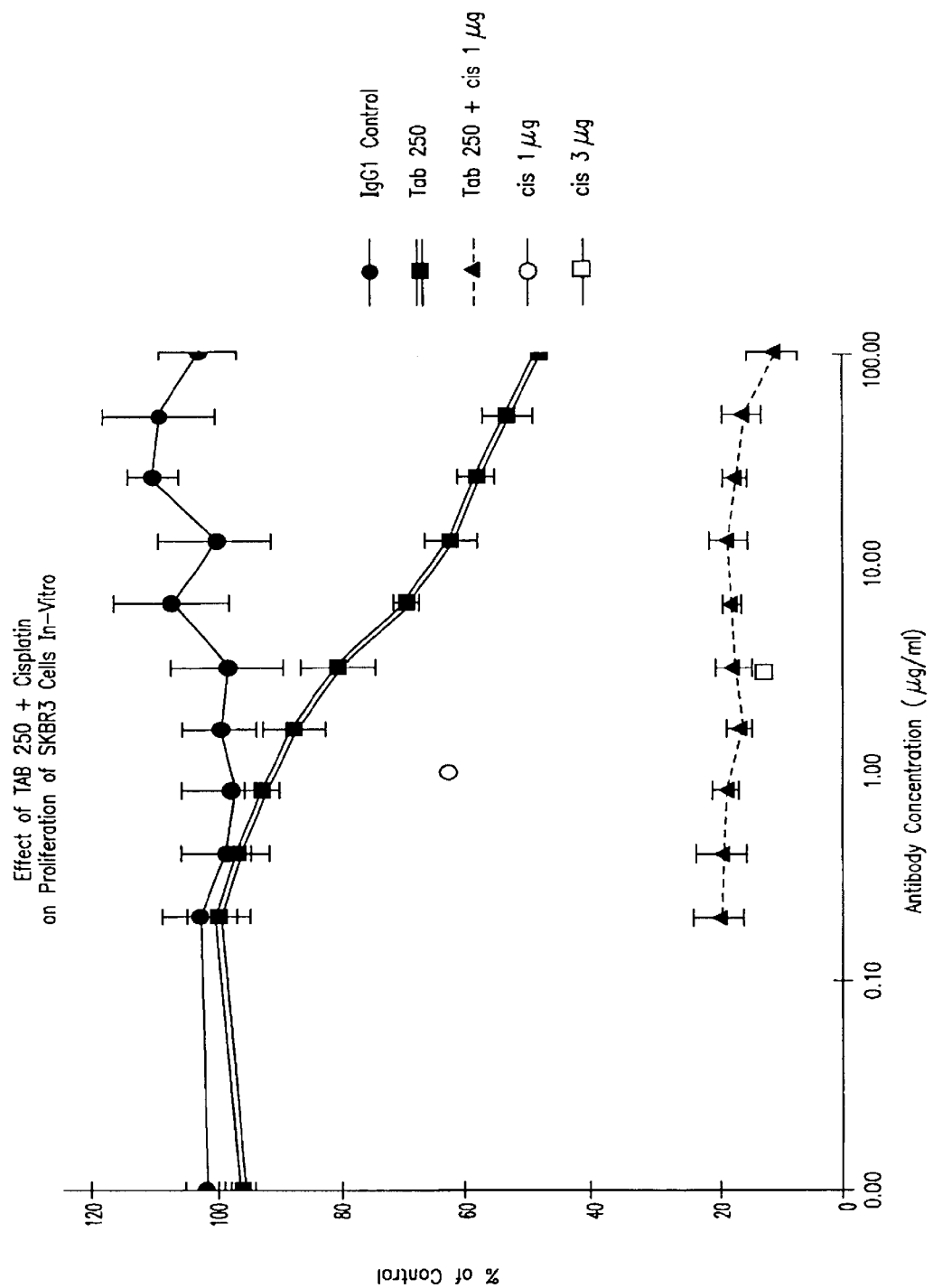
FIG. 2 shows the effect of a particular monoclonal antibody to c-erbB-2 (TAb 250) in combination with cisplatin (cisplatinum) on the proliferation of SKBR3 cells. The addition of a non-specific IgG1 isotype antibody (Chemicon International Inc.), which served as a control, did not inhibit the growth of the cells. The use of TAb 250 by itself inhibited proliferation of the cells up to 50% at a concentration of 100 micrograms per milliliter ($\mu$g/ml). At a concentration of 0.8 $\mu$g/ml of antibody there was no significant difference between the proliferation of cells treated with TAb 250 and those cells treated with the nonspecific IgG1 antibody. However, when the cells were exposed simultaneously to the TAb 250 antibody and 1.0 $\mu$g of cisplatin, extensive inhibition of cell growth occurred at all antibody concentrations. At 1.0 $\mu$g of cisplatin alone the growth of the cells was reduced to 65% of control, whereas the combination of 1.0 $\mu$g of cisplatin and as little as 0.19 $\mu$g/ml of TAb 250 inhibited growth to 15–20% of control. The use of 3.0 $\mu$g of cisplatin alone is highly toxic to the cells, so addition of antibody does not significantly enhance the effect.
Figure 3:
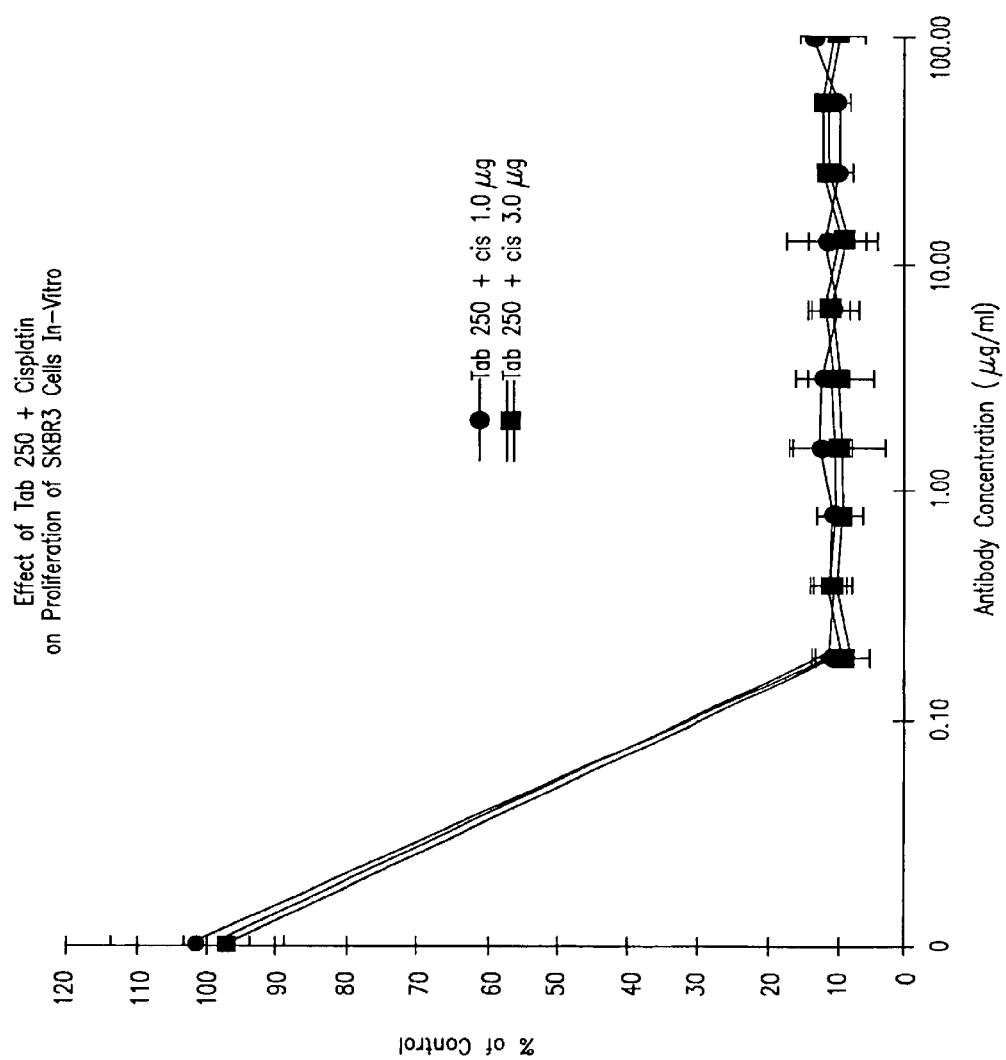
FIG. 3 shows that SKBR3 cells treated with the combination of a c-erbB-2 antibody (TAb 250) and cisplatin for three days followed by incubation in fresh growth medium for an additional five days are unable to resume proliferation as measured by the MTT assay suggesting that the combination is cytotoxic.

The individual and combined effects of cisplatin and TAb 250, another anti-c-erbB-2 monoclonal antibody, on the growth of SKBR3 cells are shown in FIG. 2. By itself, TAb 250 inhibited proliferation up to 50% at a concentration of 100 µg/ml. This effect decreased with dilution of the antibody such that at 0.8 µg/ml there was no significant difference between proliferation of TAb 250 treated cells and those treated with a nonspecific IgG1 isotype antibody. In contrast, cells that were exposed simultaneously to both TAb 250 and 1.0 µg of cisplatin showed extensive inhibition of cell growth at all antibody dilutions. At 1.0 µg, cisplatin alone reduced cell growth to 65% of control, whereas cells treated with both 1.0 µg cisplatin and as little as 0.19 µg/ml TAb 250 were inhibited to 15–20% of control. FIG. 3 shows that these cells were unable to resume proliferation after an additional week in culture in the absence of cisplatin and antibody; therefore, these cells are considered killed.

Also shown in FIG. 2 is the effect of 3.0 µg of cisplatin alone and in combination with antibody. Because this concentration of cisplatin is so highly toxic to the cells, there is no additional antibody effect.

Several other monoclonals made against c-erbB-2 were also tested for growth inhibition alone and in combination with cisplatin (Table 2). TAbs 250, 252, 253 and 256 all inhibited proliferation to approximately 50% of control at 100 µg/ml and 75–90% of control at 3.12 µg/ml. In combination with cisplatin, however, TAb 250 was the most effective, reducing proliferation to 16–20% of control.

TABLE 2

Effects of c-erbB-2 Monoclonal Antibodies on Proliferation of SKBR3 Cells in vitro

| | ANTIBODY | 100 µg/ml | 3.12 µg/ml |
|---|---|---|---|
| 1. | IgG1 Control + cis | 96.9 ± 4.5[1] 63 | 95.4 ± 5.2 63 |
| 2. | 250 + cis | 54.9 ± 14.7 16.7 ± 12.8 | 76.3 ± 12.0 19.3 ± 9.9 |
| | cis alone ~ 65 | | |

TABLE 2-continued

Effects of c-erbB-2 Monoclonal Antibodies on
Proliferation of SKBR3 Cells in vitro

| | ANTIBODY | 100 µg/ml | 3.12 µg/ml |
|---|---|---|---|
| | 250.05[2] + | 52.7 ± 12.2 | 74.7 ± 15.5 |
| | cis | 19.3 ± 3.2 | 22.3 ± 1.5 |
| | cis alone ~ 65 | | |
| 4. | 251 + | 71.6 ± 16.2 | 80.5 ± 7.9 |
| | cis | 39 | 34 |
| | cis alone = 44 | | |
| 5. | 252 | 55 ± 26.4 | 78.5 ± 8.6 |
| 6. | 253 | 44 ± 22.6 | 82 ± 11.3 |
| 7. | 254 | 69.3 ± 11.0 | 77.3 ± 2.6 |
| 8. | 255 | 63.4 ± 10.5 | 77.6 ± 11.6 |
| 9. | 256 + | 50.3 ± 8.6 | 75.7 ± 4.5 |
| | cis | 45 | 53 |
| | cis alone = 65 | | |
| 10. | 257 | 67 ± 8.7 | 81.7 ± 2.3 |
| 11. | 258 | 75 ± 7.0 | 82.5 ± 5.3 |
| 12. | 259 + | 73.2 ± 22.3 | 85.4 ± 4.3 |
| | cis | 57 ± 0 | 59.5 ± 3.5 |
| | cis alone = 90 | | |
| 13. | 260 + | 73.3 ± 18.5 | 90.8 ± 1.7 |
| | cis | 42.5 ± 19.1 | 46 ± 21.2 |
| | cis alone = 90 | | |
| 14. | 261 + | 88 ± 14.2 | 95.3 ± 3.8 |
| | cis | 54 | 72 |
| | cis alone = 67 | | |
| 15. | 262 + | 74 ± 12.1 | 88.3 ± 4.1 |
| | cis | 56 | 70 |
| | cis alone = 67 | | |
| 16. | 263 + | 69.8 ± 17.6 | 86.4 ± 8.6 |
| | cis | 45 ± 14.1 | 68.5 ± 4.9 |
| | cis alone = 90 | | |
| 17. | 264 | 69 ± 5.7 | 69.5 ± 2.1 |
| 18. | 265 | 61.5 ± 19.1 | 80.5 ± 7.8 |

[1]Numbers are expressed as percent of untreated control cells ± the standard deviation.
[2]This represents TAb 250 purified from a different batch.

Figure 4:
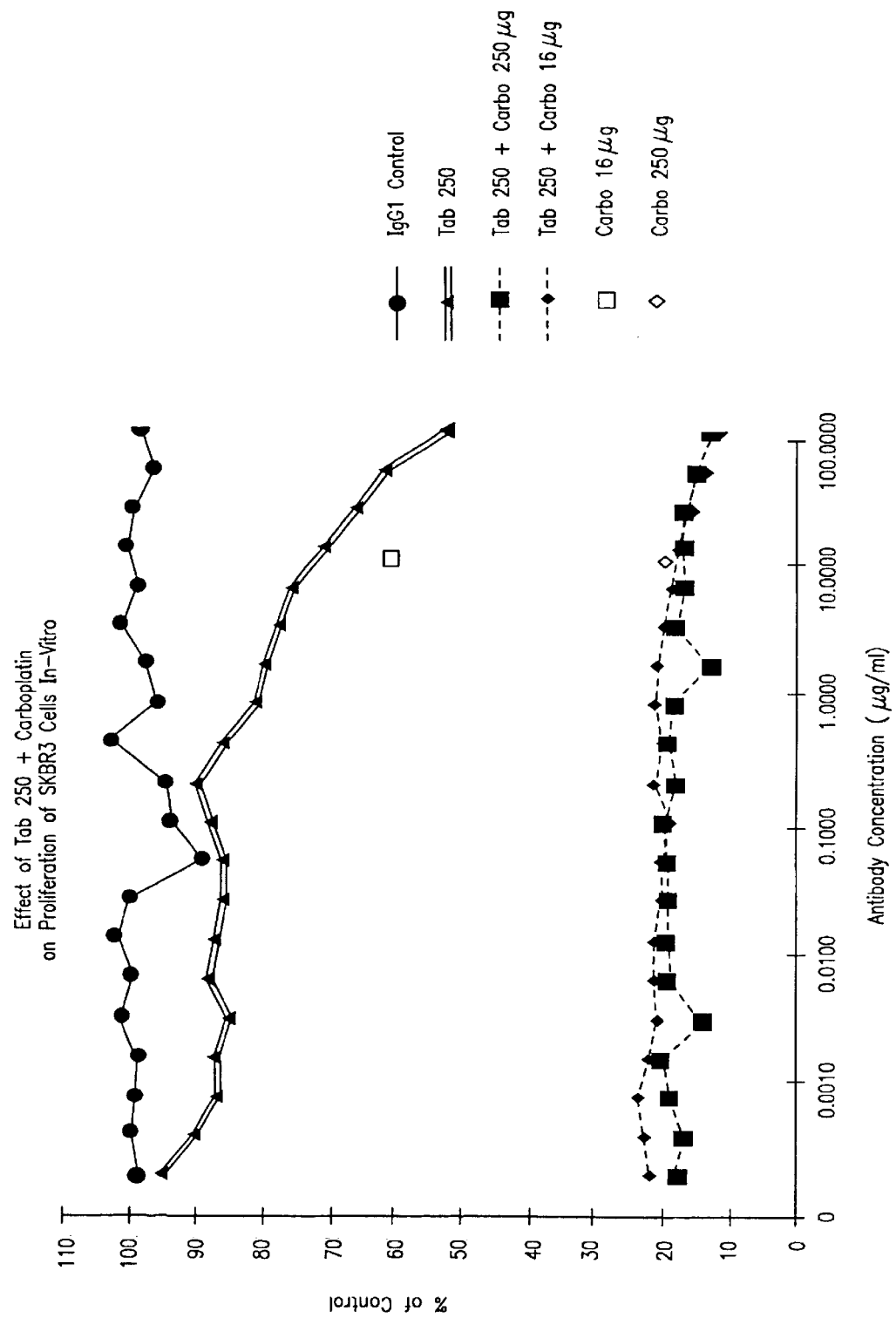
FIG. 4 shows the synergistic effects of the combination of a c-erbB-2 antibody (TAb 250) and carboplatin at a concentration of 16 $\mu$g of carboplatin.

In addition to cisplatin, two other drugs have shown significantly enhanced toxicity when exposed to cells in the presence of TAb 250. In FIG. 4, 16 µg of carboplatin reduced cell proliferation to 63% of control. When cells were treated with 16 µg carboplatin plus TAb 250 over a range of 90 pg/ml to 100 µg/ml, cell growth was inhibited to approximately 20% of control.

Figure 5:
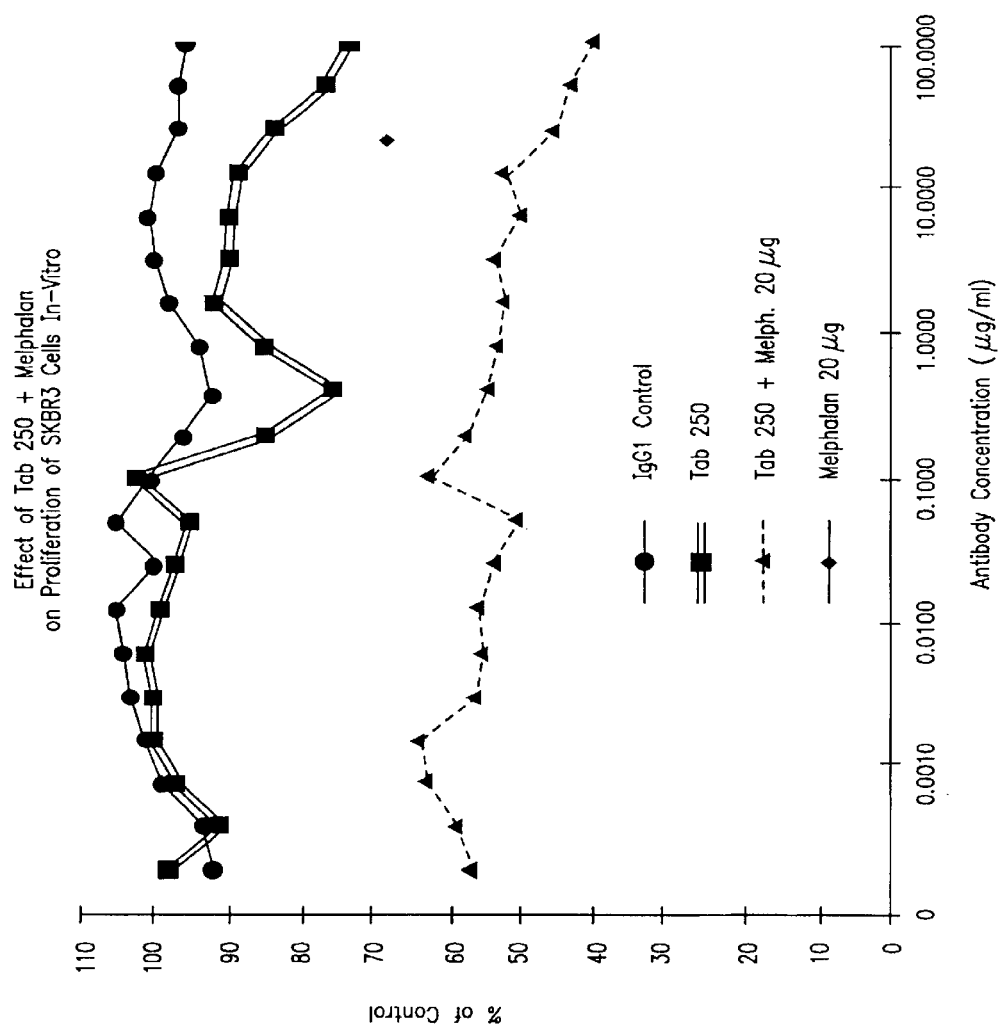
FIG. 5 shows the synergistic effects of the combination of a c-erbB-2 antibody (TAb 250) and melphalan at a concentration of 20 $\mu$g of melphalan. While 20 $\mu$g of melphalan alone reduced proliferation of the SKBR3 cells to 70% of control, the addition of doses less than 0.001 $\mu$g/ml of antibody inhibited cell growth to about 55% of control.
Figure 6A:
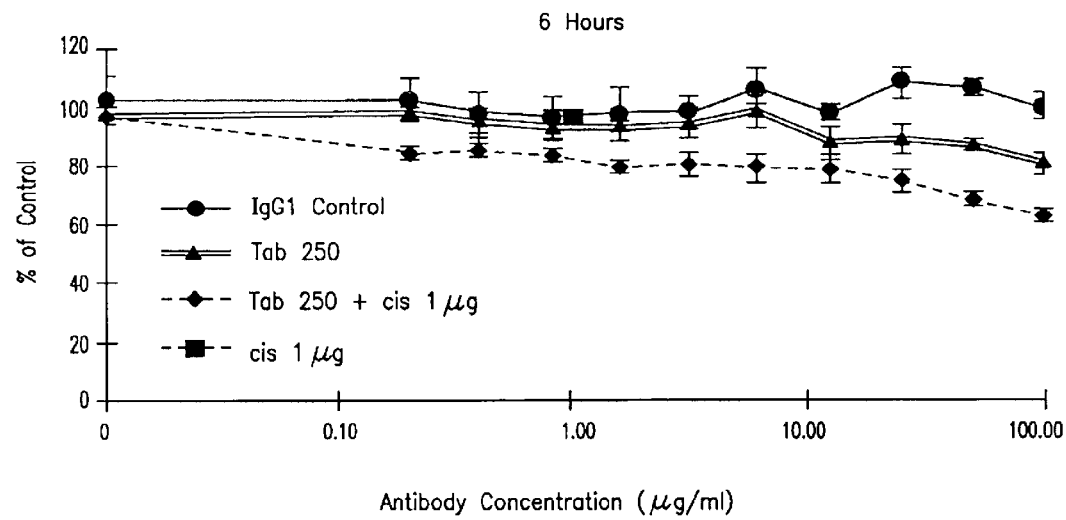
FIGS. 6A, 6B, 7A and 7B show the effect of a c-erbB-2 antibody (TAb 250) in combination with cisplatin on the proliferation of SKBR3 cells after 6, 12, 24 and 48 hours. Enhanced cytotoxicity is shown after 24 hours of treatment. The effect is even more pronounced with a 48-hour exposure of the combination.
Figure 6B:
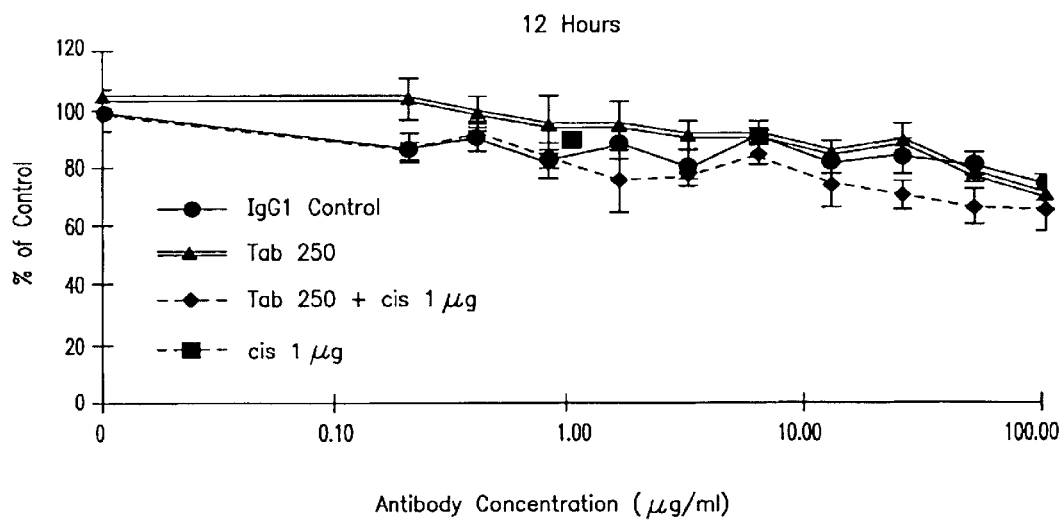
Figure 7A:
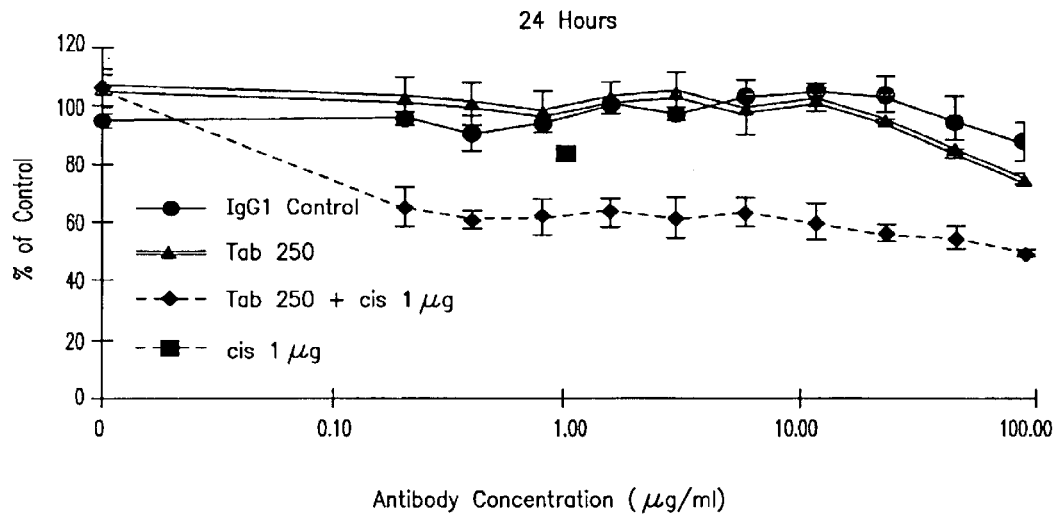
Figure 7B:
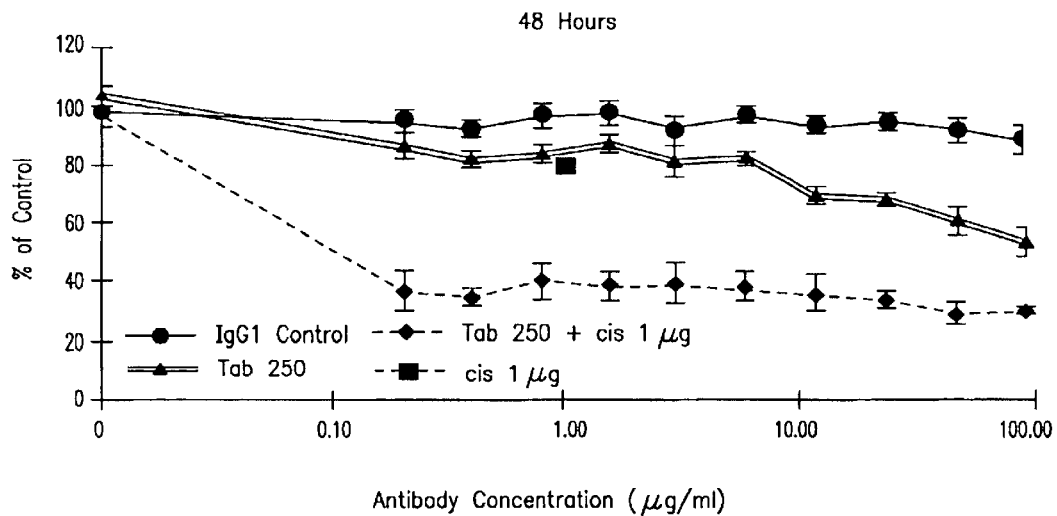

FIG. 5 shows the effects of TAb 250 combined with melphalan. While 20 µg of melphalan alone reduced proliferation to 70% of control, the addition of even as little as 90 pg/ml of antibody inhibited cell growth to approximately 55% of control. This concentration of antibody alone had no significant effect on the cells. The maximum standard deviation for any point on the melphalan plus TAb 250 curve was 5.8% of control.

One agent, cytoxan, also known as endoxan, failed to show a synergistic response in the MTT assay. It was appreciated later that the agent must be activated with a liver microsome mixed-function oxidase to produce 4-hydroxycyclophosphamide, which is the active alkylating form. In vivo, the liver would provide the enzyme to activate cytoxan. See *Principles of Cancer Treatment* (1982) Carter, S. K., Glatstein, E., and Livingston, R. (eds.), McGraw Hill, page 116.

Example 3
Time Course Study

Using the MTT assay described in Example 2, a time course study of treatment on SKBR3 cells with TAb 250 in combination with cisplatin was conducted. The SKBR3 cells were plated as described for the assay, then antibody and drug were added for 6, 12, 24, or 48 hours and then gently washed off. Each of the cultures was refed with growth media and the plates were incubated for up to 72 hours. As shown in FIGS. 6A, 6B, 7A, and 7B, the combination of TAb 250 and cisplatin had an enhanced effect after 24 hours of treatment, with a more pronounced effect after a 48-hour exposure.

Example 4
Effect of a c-erbB-2 Monoclonal Antibody and Cisplatin in Combination on Human Tumor Xenografts (0, 7, and 14 days)

SKOV3 cells were injected subcutaneously into five Balb/c nude mice at $10^7/0.2$ ml. Once the tumors reached approximately 1000 millimeters ($mm^3$), they were extracted, finely minced and reimplanted into a larger group of mice. After one week, the mice were divided into five groups of six mice each and injected as follows: Group 1—500 µg of non-specific IgG1 isotype control; Group 2—500 µg of TAb 250; Group 3—50 µg of cisplatin; Group 4—500 µg of the isotype control in combination with 50 µg of cisplatin; and Group 5— 500 µg of TAb 250 in combination with 50 µg of cisplatin. All injections were given intravenously on day 0 and in the combination treatments, antibody was injected first followed by the cisplatin 45 minutes later. Additional treatments were given at 7 and 14 days. Significant inhibition of tumor growth was observed in the mice treated with the TAb 250 and cisplatin combination in contrast to the other treatment regimens. Three of the six mice treated with this combination had no measurable tumor for up to three weeks after the last treatment. The results of this experiment are shown in FIG. 8. All animals tolerated the combined treatment well as evidenced by no loss in body weight.

The mice in the five groups described above were followed for a total of 85 days without any additional treatment being given. As shown in FIG. 9, the tumors treated with TAb 250 and cisplatin began to regrow at day 45. However, it took an additional 40 days for these tumors to reach a size equivalent to those tumors treated with cisplatin alone at day 35. The growth rate of the tumors treated with TAb 250 and cisplatin in combination never reached the rate of the groups treated with isotype antibody control or TAb 250 alone.

Example 5
Effect of a c-erbB-2 Monoclonal Antibody in Combination with Cisplatin on Human Tumor Xenografts (14, 21, and 28 Days)

In this experiment, which was conducted as described in Example 4, the mice were treated on days 14, 21, and 28 instead of days 0, 7, and 14 as in Example 4. FIG. 10 shows the results of these treatments. The combination of TAb 250 and cisplatin showed an enhanced effect and no significant tumor growth until day 50. The other treatment groups showed little effect on tumor growth.

Example 6
Anti-proliferative Effects of TAb250 on SKBR3 and SKVO3 Cells
A. TAb 250 and Cisplatin Effect The effects of TAb 250 alone and in combination with cisplatin (CDDP) on growth of human tumor cells in soft agar was assessed. SKOV3 (6,000 cells per ml) or SKBR3 (12,000 cells per ml) were incubated in assay medium (DMEM:F12, University of California at San Francisco Cell Culture Facility), 10% dialyzed FBS 0.1 mM nonessential amino acids in solution obtained from Gibco, 1 mM sodium pyruvate and 10 mM HEPES) for 30 minutes at 37° C. with 1 or 10 µg/ml TAb 250. CDDP at concentrations of either 10 ng/ml for SKBR3 cells and 100 ng/ml for SKOV3 cells was then added and the incubation continued for 1.5 hours at 37° C. An equal volume of assay medium containing 0.8% Sea Plaque agarose and appropriate concentrations of TAb 250 and CDDP were combined with the cell mixture. Triplicate 1 ml aliquots were dispensed onto base layers of 0.8% agarose in assay medium containing the appropriate amounts of TAb 250, CDDP or both, in 35 mm dishes. After 14 days at 37° C./5% $CO_2$ in a humidified chamber, viable colonies were stained for 24 hours with Nitro Blue tetrazolium dye (Sigma, 500 µg in 1 ml PBS). Stained colonies greater than 60µ were scored positive using a FAS III Image Analysis System (Bausch and Lomb, Rochester, N.Y.). The data are expressed as a percentage of untreated control colonies formed. See FIG. 11. In control dishes, SKOV3 and SKBR3 cells formed 859+/−16 and 1107+/−72 colonies, respectively. See FIG. 11. For SKBR3 cells, 10 ng/ml cisplatin did not inhibit colony formation. However, the combination of cisplatin and TAb 250 inhibited colony formation 52% and 32% of control compared with 62% and 46% of control for TAb 250 alone. For SKOV3 cells, TAb 250 alone had little effect on colony formation. However, the inhibitory effects of TAb 250 and cisplatin on colony formation was 20–30% greater than for cisplatin alone.

Example 7

Binding Characteristics

A. Preparation and Handling of $^{125}$I-TAb 250

TAB 250 was radiolabeled using Iodobeads (Pierce) according to the manufacturer's specifications. Carrier-free Na$^{125}$I (400 uCi of IMS.30, Amersham) was reacted with 25 ug TAb 250 in 100 mM Na-phosphate buffer (200 ul, pH 7.4) in the presence of 3 Iodobeads. This resulted in an approximate ratio of one iodine atom per IgG molecule. The incorporation was allowed to proceed at room temperature for 7.5 minutes with intermittent mixing. The reaction mixture was removed from the beads, and after 5 minutes, the volume was adjusted to 0.5 ml with Na-phosphate buffer and 2 ul were taken to estimate specific activity (see below). The remaining volume was de-salted by gel filtration using a NAP-5 column (Pharmacia) equilibrated with PBS containing 0.1% BSA and 0.02% azide. The radiolabeled antibody was eluted in 1 ml column buffer and was stored at 4C for up to 6 weeks with no apparent loss of binding activity. The de-salted material was essentially free of unincorporated iodine since >95% was TCA-precipitable.

The specific activity of the radiolabeled antibody was estimated by TCA precipitation of the material before the de-salting step. Thus, 2 ul of the reaction mixture was diluted 500-fold in column buffer and duplicate aliquots mixed with an equal volume of ice-cold 20% TCA. After 15 minutes on ice the precipitated material was collected by centrifugation (10 min, 3000×g). Supernatants and pellets were counted separately, and the incorporation was expressed as the percent of TCA-precipitable counts. The incorporation obtained in separate iodinations ranged from 27% to 45%, yielding specific activity estimates from 3.9 to 7.2 uCi/ug. Before each binding experiment, an appropriate amount of $^{125}$I-TAb 250 was de-salted by gel filtration using a NAP-5 column equilibrated in binding buffer. This procedure removed the azide and yielded material that was routinely >98% TCA-precipitable.

B. Time Course of $^{125}$I-TAb 250 Binding

To determine the time course and temperature dependence of $^{125}$I-TAb 250 binding, SKBR3 cells were removed from culture flasks with calcium-magnesium free PBS containing 2 mM EDTA and 1% glucose. The cells were collected by centrifugation, washed once and resuspended to yield 100,000 cells/ml in MEM plus 0.1% BSA buffered with 50 mM HEPES, pH 7.4 (binding buffer). To individual aliquots $^{125}$I-TAb 250 (approximately 80,000 cpm/ml) was added alone (total binding) or with excess unlabeled TAb 250 (50 ug/ml, non-specific binding). The reaction mixtures were incubated at 22° C., 37° C., or on ice and at the time points indicated in FIG. 14A, triplicate 100 ul aliquots of the cells were pelleted and washed in 800 ul of ice-cold binding buffer. The supernatants were aspirated and the cell-associated radioactivity was determined using an Isodata gamma counter (Rolling Meadows, Ill.). Specific binding is defined as total binding cpm minus nonspecific binding cpm, and is expressed as a percentage of total counts added. FIG. 12A indicates that the binding of $^{125}$I-TAb 250 is both time and temperature dependent, and that equilibrium is reached and maintained after 2 to 3 hours on ice. SKOV3 cells demonstrated a similar time course of $^{125}$I-TAb 250 binding using the same procedure (data not shown).

C. Determination of TAb 250 Binding Sites in Cells

Using the equilibrium binding conditions defined in 7B, SKBR3 cells were incubated in the presence of $^{125}$I-TAb 250 alone, or in combination with increasing amounts of unlabeled TAb 250 (see FIG. 12B). The assay was terminated as described in Example 7B. To approximate the number and affinity of TAb 250 binding sites, these data were analyzed using the computerized program LIGAND (Munson and Rodbard, Anal. Biochem., 1980, available from the authors). The resultant linear Scatchard plot is represented in FIG. 12C and indicates a single class of binding sites present in SKBR3 cells. Similar results were obtained using SKOV3 cells. Based on the assumption that TAb 250, an IgG molecule, binds bivalently, the binding capacity in SKBR3 or SKOV3 cells was estimated to be $2 \times 10^6$ sites/cell or $7 \times 10^5$ sites/cell, respectively. Both cell lines demonstrated dissociation constants between 0.2–0.5 nM. See FIGS. 12B and C.

Example 8

Binding Analyses

A. Down Modulation

SKBR3 or SKOV3 cells were plated in 96-well dishes (Costar) at 10,000 to 14,000 cells per well in growth medium. After 24 hr at 37° C., TAb 250 was added alone or in combination with 1 µg/ml CDDP. Following an additional 24 hours, the monolayers were washed twice with PBS and either used immediately (FIG. 13A) or allowed to "recover" in growth medium for 24 hours (FIG. 13B) before the binding analyses. A time course for down modulation is shown in FIG. 13C. $^{125}$I-TAb 250 binding reactions were conducted in 100 µl of binding medium containing $^{125}$I-TAb 250 at concentrations of about 0.6 ng/ml with or without excess unlabeled TAb 250. To terminate the binding reaction, medium was aspirated, and each well was washed three times with 200 µl of ice-cold binding buffer. The monolayers were solubilized in 100 µl of 0.1 M NaOH with 2% $Na_2CO_3$ plus 1% SDS and the lysates were transferred to counting tubes using a Skatron Harvesting device (Skatron, Inc., Sterling, Va.).

These data demonstrate that after a 24-hour exposure to TAb 250, human tumor cells that express c-erbB-2 protein lose the ability to bind $^{125}$I-TAb 250. This loss of receptor-ligand interaction was dose-dependent (FIG. 13A), and was fully reversible when the cells were allowed to recover for 24 hours in the absence of TAb 250 (FIG. 13B). Neither the down-modulation nor the recovery of $^{125}$I-TAb 250 binding was influenced by the presence of 1 ug/ml cisplatin (FIGS. 13A and B), indicating that under the conditions of these assays the drug did not effect the c-erbB-2 protein. In contrast, further studies showed that down-modulation of $^{125}$I-TAb 250 binding was evident after a 40 minute treatment with TAb 250 (FIG. 13C).

B. Internalization of TAb 250.

To determine internalization of TAb 250, SKBR3 and SKOV3 cells were harvested as described in Example 7A above and resuspended in ice-cold binding buffer (described above) containing $^{125}$I-TAb 250. After the cell surface binding of the radiolabel reached equilibrium (3 hours on ice), the cells were pelleted (800×g for 10 minutes, 40° C.) and washed twice with ice-cold binding buffer in order to remove unbound antibody. The cell pellets were resuspended in ice-cold binding medium and aliquots were taken to determine the amount of initial $^{125}$I-TAb 250 surface binding. To initiate internalization of the radioligand, the cells were warmed to 37° C. and aliquots collected by centrifugation (800×g, 15 minutes, 40° C.) at the times indicated in FIG. 14. The supernatants which contained dissociated or recycled antibody were collected. The pellets were resuspended twice in an acid wash (100 µl/tube PBS, 1% glucose, pH 1). Supernatants containing surface-bound antibody were combined and counted. The tips of the tubes containing the remaining cell-associated radioactivity were clipped and counted. Data in FIG. 14 are expressed as a percentage of the initial (before warming to 37° C.) surface bound cpm. Control studies showed that the cell viability, as judged by trypan blue exclusion, was not affected by the procedure. A method for determining internalization of the ligand-receptor complex is described in Haigler, et al., *J. Biol. Chem.*, 255:1239–1241 (1980).

C. Receptor Turnover

Receptor turnover was measured in SKBR3 cells grown to confluence in MEM containing 10% FBS and 2 mM glutamine. Following labeling for 5 hours with 160 µCi/ml Trans$^{35}$S-label (ICN, Irvine, Calif.), the cells were washed twice with MEM, and then incubated in fresh medium with or without 10 µg/ml TAb 250. After incubation for the indicated times, the cells were washed with PBS and lysed in RIPA buffer (50 mM Tris-HCl pH 7.4, 150 mM NaCl, 1% NP-40 (Sigma), 1% sodium deoxycholate, 0.5% SDS plus protease inhibitors (0.2 mM PMSF, 0.5 ug/ml leupeptin, 0.7 ug/ml pepstatin)). The samples were then centrifuged at 100,000×g for 30 min. Supernatants were immunoprecipitated with either non-immune IgG (FIG. 15A, lanes 2 and 15) or TAb 250 (FIG. 15A, lanes 3–14) followed by electrophoresis on a 7.5% SDS-PAGE and autoradiography. Lanes 2–8 in FIG. 15A represent immunoprecipitates from cells chased in medium alone while lanes 9–15 represent immunoprecipitates from cells chased in medium containing 10 µg/ml TAb 250. The autoradiograph was scanned with a laser densitometer (Shimadzu Corp., Kyoto, Japan) and relative peak intensity (RPI) plotted against time of chase. See FIG. 15B. The amount of c-erbB-2 protein did not decrease after a 1 hour chase in medium without TAb 250 while there was a greater than 10-fold decrease in c-erbB-2 protein by 1 hour when incubated with 10 µg\ml of TAb 250; therefore, the turnover of c-erbB-2 in SKBR3 cells appears to be increased by the addition of TAb 250 to the culture medium.

D. Receptor Phosphorylation

Receptor phosphorylation was determined in SKBR3 cells grown to confluence and serum-starved for 48 hr prior to labeling with $^{32}$P-orthophosphate. Following labeling, cells were incubated with 10 µg/ml of TAb 250 for the times indicated in FIG. 16. Labeling medium was removed, cells were washed twice with PBS and lysed in RIPA buffer containing protease and phosphatase inhibitors. Lysates were centrifuged at 100,000×g for 30 min and immunoprecipitations were carried out using a polyclonal anti-peptide which is directed against the C-terminus of the c-erbB-2 protein. However, other anti-c-erbB-2 antibodies can be used as well. Samples were analyzed by SDS-PAGE and autoradiography. Following autoradiography, the gel was treated with 1 M KOH for 2 hr at 55° C., dried under heat and vacuum, and re-exposed to film. See FIG. 16. The results suggest that the phosphorylation occurs on tyrosine residues as it was stable to base hydrolysis by KOH (see Cooper, et al., supra).

SKBR3 and SKOV3 cells bind $^{125}$I-TAb 250 with high affinity ($K_D$<1 nM) and these cells exhibit a large receptor capacity (2×10$^6$ and 7×10$^5$ sites/cell, respectively). Furthermore, the c-erbB-2 protein was down modulated in a dose-dependent manner in both SKBR3 and SKOV3 cells and this down modulation was not affected when TAb 250 was used in combination with CDDP. Down modulation occurred rapidly as treatment of SKBR3 cells with TAb 250 for 40 min resulted in a greater than 10-fold decrease in the ability of the cells to bind $^{125}$I-TAb 250. Down modulation appeared to be due to degradation of the receptor since immunoprecipitation of $^{35}$S-labeled cells showed a greater than 10-fold decrease in precipitable receptor by 1 hr. When antibody was removed from the cells, the c-erbB-2 protein reappeared on the cell surface by 24 hr. This recovery was similar in cells that received either TAb 250 alone or TAb 250 with CDDP. Studies examining the internalization of TAb 250 demonstrated that approximately 30% and 20% (SKBR3 and SKOV3 cells, respectively) of the antibody was internalized after 3 hr at 37° C. Treatment of SKBR3 cells with TAb 250 resulted in a ~5-fold increase in the phosphorylation of c-erbB-2. $^{32}$P-labeled c-erbB-2 from cells treated with TAb 250 was stable to base hydrolysis suggesting that phosphorylation was on tyrosine residues.

Example 9

TAb 250-like Antibodies

A. $^{125}$I-TAb 250 Competition Assay

A variety of monoclonal antibodies raised against the c-erbB-2 protein were tested for their ability to influence the binding of $^{125}$I-TAb 250 (FIGS. 17A and B). Thus, SKOV3 cells (100,000 cells/ml in binding buffer, Example 7A) were incubated in the presence of $^{125}$I-TAb 250 alone, or in combination with 1 or 10 ug/ml of the antibodies noted. After 60 minutes at 37° C. (see FIG. 12A) the assay was terminated by centrifugation as described in Example 7A. As shown in FIGS. 17A and B, the different antibodies displaced $^{125}$I-TAb 250 binding to varying degrees. Several monoclonal antibodies displayed TAb 250-like activity in this binding assay. For example, TAbs 251, 252, 256, and 257 (FIG. 17A) inhibited $^{125}$I-TAb 250 binding at concentrations equivalent to TAb 250, indicating that the binding of $^{125}$I-TAb 250 to its epitope was influenced by the interaction of these antibodies with their respective epitopes. In contrast, TAb 260 (FIG. 17A), TAbs 261, 263, and 264 (FIG. 17B) did not inhibit the binding of $^{125}$I-TAb 250, suggesting that the binding site(s) for these antibodies are distinct from the TAb 250 binding site. These data are further summarized in Table 3.

The following Table 3 sets forth the ability of other monoclonal antibodies described in Example 1, and others raised similarly, to displace TAb 250 in a competitive binding assay using SKOV3 cells (see the first and second columns). The second column of the Table reports whether the binding displacement was positive, negative or poor.

TABLE 3 c-erbB-2 MAb Characterizations

| Antibody | | Displacement of $^{125}$I-TAb 250 | PO$_4$ in vitro | PO$_4$ in vivo |
|---|---|---|---|---|
| TAb | 250 | pos | pos | pos |
|  | 251 | pos | pos | pos |
|  | 252 | pos | pos | ND |
|  | 253 | pos | neg | ND |
|  | 254 | pos | pos | ND |
|  | 255 | pos | neg | ND |
|  | 256 | pos | pos | ND |
|  | 257 | pos | neg | ND |
|  | 258 | pos | pos | ND |
|  | 259 | pos | pos | neg |
|  | 267 | pos | ND | ND |
| TAb | 260 | neg | ND | neg |
|  | 261 | neg | neg | neg |
|  | 262 | neg | ND | ND |
|  | 263 | neg | ND | pos |
| TAb | 264 | poor | pos | ND |
|  | 265 | poor | ND | ND |
|  | 266 | poor | ND | ND |
|  | 268 | poor | ND | ND |
|  | 269 | poor | ND | ND |
|  | 270 | poor | ND | ND |

B. In Vitro Autophosphorylation Assay

To compare the effects of anti-c-erbB-2 monoclonal antibodies on the autophosphorylation of the c-erbB-2 protein, an in vitro autokinase reaction was carried out using lysates derived from NIH3T3 cells expressing high levels of human c-erbB-2 (3T3$_t$). Cells were lysed in buffer containing 50 mM Tris HCl, pH 7.4, 0.15 M NaCl, 1% NP-40, 0.5% DOC (sodium deoxycholate), 1 mM EDTA (HO buffer) plus protease and phosphatase inhibitors (10 mM NaF, 50 uM NaVO$_4$). After centrifugation at 100,000×g for 30 min, the lysates were immunoprecipitated with antibody TAbs 250, 251, 257, 259 or 261 (see FIG. 18) and as indicated in column 3 of Table 3. Following extensive washing of the immune complexes in HO buffer containing 1 M NaCl, then HO buffer alone, and finally PBS, the pellets were incubated with 20 mM Pipes, pH 7.4, 10 mM MnCl$_2$, and 10 $\mu$Ci $\gamma^{32}$P-ATP (ICN, Irvine, Calif.) for 30 min at 22° C. The samples were analyzed by SDS-polyacrylamide gel electrophoresis and autoradiography. The extent of the phosphorylated c-erbB-2 protein was measured with a laser densitometer and compared to the intensity of the protein band following immunoprecipitation of $^{35}$S-labeled 3T3$_t$-cell lysates as an internal control for comparing the amount of autophosphorylation induced by each antibody. The procedure for $^{35}$S-labeling and immunoprecipitation is described in Example 8C above. The extent of autophosphorylation induced by the antibodies varied over 70-fold. The ratio of $^{32}$P:$^{35}$S for TAbs 250, 251 and 259 was 1.5, 1.4 and 2.2 respectively, compared to 0.1 and 0.03 for TAbs 257 and 261.

C. In Vivo Phosphorylation Assay

The effects of anti-c-erbB-2 monoclonal antibodies on the phosphorylation of p185 c-erbB-2 was also compared by in vivo labeling with $^{32}$P-orthophosphate and immunoprecipitation. Following labeling of 3T3$_t$ cells for 16 hr., lysates were immunoprecipitated with anti-c-erbB-2 antibodies TAbs 251, 259, 260, 261 and 263 (see FIG. 19), and as indicated in column 4 of Table 3. Following immunoprecipitation, the samples were analyzed by SDS-polyacrylamide gel electrophoresis and autoradiography. The extent of the phosphorylated c-erbB-2 protein was measured by laser densitometry and compared to the intensity of the protein band following immunoprecipitation of $^{35}$S-labeled cell lysates. The extent of phosphorylation following immunoprecipitation of $^{32}$P-labeled cell lysates varied by >90-fold. While the ratio of $^{32}$P:$^{35}$S for TAbs 251 and 263 was 4.0 and 9.2 respectively, the 32P:35S ratio was only 0.6, 0.1, and 0.2 for TAbs 259, 260, and 261 respectively.

D. Tumor Cell Proliferation Assay

To determine the effect of various antibodies reactive with the c-erbB-2 protein on tumor cell proliferation, SKOV3 cells were seeded in growth medium into 24-well dishes at 10,000 cells/well. After 24 hr at 37° C., monoclonal antibodies (TAbs 250, 251, 257, 261, 263) or purified Fab or F(ab')$_2$ fragments of TAb 250 were added to yield a final assay concentration of 10 $\mu$g/ml. Ten days after the addition of antibodies, the cells were removed with trypsin and quantified using a Coulter Counter. In addition, representative cell samples were stained with propidium iodide and analyzed using a FACS Scan (Becton-Dickinson, Mountain view, Calif.) to determine the percentage of viable cells in each treatment group. Thus, each bar on FIG. 20 represents the mean of triplicates and is expressed as a percentage of the viable cell number compared to untreated control wells. Neither the number nor the viability of cells treated with TAbs 261, 263, or the FAb fragment of TAb 250 was different from untreated controls. However, after 10 days in the presence of TAbs 250, 251, or 257, the proliferation of SKOV3 cells was suppressed to 69%, 64% or 60% of control cell number. Treatment with F(ab')$_2$ fragments of TAb 250 reduced cell growth to 76% of control levels. While control cells were assessed to be >98% viable, cells treated with these antibodies demonstrated a small but significant loss of viability (from 84 to 89%).

What is claimed is:

1. A drug combination cytotoxic to tumor cells expressing c-erbB-2 protein comprising (a) an anti-neoplastic agent and (b) a molecule, not conjugated to the anti-neoplastic agent, that binds said c-erbB-2 protein on the tumor cells and induces an increase in the phosphorylation of c-erbB-2 protein when placed in contact with the tumor cells wherein said molecule it T Ab 250 or fragments thereof.

2. The drug combination of claim 1 wherein the molecule further causes down modulation of the c-erbB-2 protein.

3. The drug combination of claim 1 wherein the molecule further causes internalization of the c-erbB-2 protein.

4. The drug combination of claim 1 wherein the molecule is an anti-c-erbB-2 antibody.

5. The drug combination of claim 1 wherein the anti-neoplastic agent is an alkylating agent.

6. The drug combination of claim 1 wherein the anti-neoplastic agent is cisplatin.

7. The drug combination of claim 1 wherein the molecule is a monoclonal antibody or fragments thereof.

8. The drug combination of claim 1 wherein the molecule binds breast and ovarian tumor cells.

9. The drug combination of claim 1 wherein the combination is synergistic.

10. A method for killing target tumor cells comprising contacting the target cells with a drug combination of (a) an anti-neoplastic agent and (b) a molecule that binds said c-erbB-2 protein on test tumor cells and induces an increase in the phosphorylation of c-erbB-2 protein when placed in contact with test tumor cells wherein said molecule is T Ab 250 or fragments thereof.

11. The method of claim 10 wherein the target cells are breast tumor cells.

12. The method of claim 10 wherein the target cells are ovarian tumor cells.

13. The method of claim 10, wherein the molecule further causes down modulation of the c-erbB-2 protein.

14. The method for treating a mammal suspected of having target tumor cells expressing c-erbB-2 protein comprising administering to such mammal a therapeutic amount of a drum combination of (a) an anti-neoplastic agent and (b) a molecule that in vitro binds to said c-erbB-2 protein on said target tumor cells, and induces an increase in the phosphorylation of the c-erbB-2 protein of said tumor cells wherein said molecule is T Ab 250 or fragments thereof.

15. The method of claim 14 wherein the target tumor cells are breast tumor cells.

16. The method of claim 14 wherein the target tumor cells are ovarian tumor cells.

17. The method of claim 14 wherein the molecule further causes down modulation of the c-erbB-2 protein.

18. The method of claim 14 wherein the molecule is an antibody and the anti-neoplastic agent is an alkylating compound.

19. The method of claim 14 wherein the molecule further causes internalization of the c-erbB-2 protein.

20. The method of claim 14 wherein the drug combination is administered in synergistically effective amounts.

21. A pharmaceutical composition comprising the combination of claim 1 and a pharmaceutically acceptable carrier.

* * * * *

UNITED STATES PATENT AND TRADEMARK OFFICE
CERTIFICATE OF CORRECTION

PATENT NO. : 6,884,418 B1
APPLICATION NO. : 07/644361
DATED : April 26, 2005
INVENTOR(S) : Laura K. Shawver It is certified that error appears in the above-identified patent and that said Letters Patent is hereby corrected as shown below:

Column 26, line 40 reads "it", should read --is--
Column 27, line 6 reads "drum", should read --drug--

Signed and Sealed this

Eleventh Day of November, 2008

JON W. DUDAS
*Director of the United States Patent and Trademark Office*